United States Patent
Luo et al.

(10) Patent No.: US 11,053,258 B2
(45) Date of Patent: Jul. 6, 2021

(54) PYRIMIDINE CARBOXAMIDES AS GSK-3 INHIBITORS

(71) Applicant: BRISTOL-MYERS SQUIBB COMPANY, Princeton, NJ (US)

(72) Inventors: Guanglin Luo, Newtown, PA (US); Prasanna Sivaprakasam, Lawrenceville, NJ (US); Gene M. Dubowchik, Middlefield, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 108 days.

(21) Appl. No.: 16/463,603

(22) PCT Filed: Nov. 27, 2017

(86) PCT No.: PCT/US2017/063232
§ 371 (c)(1),
(2) Date: May 23, 2019

(87) PCT Pub. No.: WO2018/098413
PCT Pub. Date: May 31, 2018

(65) Prior Publication Data
US 2020/0181170 A1    Jun. 11, 2020

Related U.S. Application Data

(60) Provisional application No. 62/426,629, filed on Nov. 28, 2016.

(51) Int. Cl.
*C07D 498/18* (2006.01)
*C07D 471/22* (2006.01)
*C07D 498/22* (2006.01)
*A61P 25/28* (2006.01)
*A61P 25/16* (2006.01)
*A61P 25/14* (2006.01)

(52) U.S. Cl.
CPC ......... *C07D 498/18* (2013.01); *C07D 471/22* (2013.01); *C07D 498/22* (2013.01)

(58) Field of Classification Search
CPC ... C07D 471/22; C07D 498/18; C07D 498/22
See application file for complete search history.

(56) References Cited

FOREIGN PATENT DOCUMENTS

| WO | WO2009014637 A3 | 3/2009 |
| WO | WO2015069594 A1 | 5/2015 |

OTHER PUBLICATIONS

Luo, et al., Journal of Medicinal Chemistry 2016 59(3),1041-1051.

*Primary Examiner* — Susanna Moore
(74) *Attorney, Agent, or Firm* — Elliott Korsen; Shrikant M. Kulkarni

(57) ABSTRACT

The disclosure generally relates to compounds of formula I, including their salts, as well as compositions and methods of using the compounds to treat disorders associated with GSK-3.

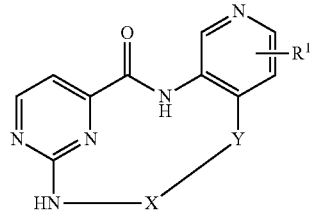

9 Claims, No Drawings

PYRIMIDINE CARBOXAMIDES AS GSK-3 INHIBITORS

CROSS REFERENCE TO RELATED APPLICATION

This application claims the priority of U.S. provisional Ser. No. 62/426,629 filed Nov. 28, 2016 which is herein incorporated by reference.

BACKGROUND OF THE INVENTION

The disclosure generally relates to compounds of formula I, including their salts, as well as compositions and methods of using the compounds. The compounds inhibit GSK-3 and may be useful for the treatment of various disorders of the central nervous system.

GSK-3 is a proline directed serine/threonine kinase that carries out the phosphorylation of multiple protein substrates. Many of these proteins are involved in the regulation of numerous diverse cellular functions, including metabolism, differentiation, proliferation and apoptosis. GSK-3 is constitutively active, with its base level of activity being positively modulated by phosphorylation on Tyr216/219, depending on isoform. GSK-3 has a unique substrate selectivity profile that is distinguished by the strong preference for the presence of a phosphorylated residue optimally located four amino acids C-terminal to the site of GSK-3 phosphorylation. Most commonly, GSK-3 activity is associated with inducing a loss of substrate function, such that GSK-3 inhibition will frequently result in increased downstream substrate activity.

GSK-3 exists in two isoforms, GSK-3a (51 kDa) and GSK-3β (47 kDa), that share 84% overall identity and greater than 98% identity within their respective catalytic domains. Both primary isoforms are ubiquitously expressed, with high levels observed in the brain, particularly in the cortex and hippocampus. In most brain areas, GSK-3β is the predominant isoform. However, some studies suggest that GKS-3α and GSK-3β share very similar, if not entirely redundant functions in a number of cellular processes. The activity of GSK-3β is significantly reduced by phosphorylation at Ser9 in the N-terminal domain, most notably by protein kinase B (PKB or AKT). This inhibitory pathway has been proposed to result in neuroprotection, neurogenesis, and favorable outcomes following pharmacological treatment in various mood disorders.

Alzheimer's disease (AD) pathology is prominently associated with the formation of beta-amyloid (Aβ) plaques, soluble forms of Aβ such as Aβ1-42 that are associated with increased neuronal toxicity, and neurofibrillary tangles (NFTs). There is evidence to suggest that certain pathological mechanisms in AD, such as Aβ1-42, cause increases in GSK-3 activity in the brain. A principal consequence of this dysregulation is the hyperphosphorylation of the microtubule associated protein tau. This function of GSK-3 has been demonstrated both in cell culture, and in in vivo studies looking at tau and NFT formation. Hyper-phosphorylated tau disengages from microtubules resulting in structural destabilization of microtubules with concomitant negative effects on intracellular structures and transport mechanisms. In addition, the uncomplexed hyperphosphorylated tau assembles into paired helical filaments (PHFs) that aggregate to produce the stereotypic intracellular NFTs associated with AD. Other potential pathological consequences of over-activation of GSK-3 include neuroinflammation and neuronal apoptosis. In addition, GSK-3 has been demonstrated to be involved in mechanisms underlying memory and learning, and dysregulation of GSK-3 function may explain some of the early cognitive deficits observed in AD.

GSK-3 is also known to play a key role in glucose metabolism, and was first identified as the enzyme responsible for effecting the inhibitory phosphorylation of glycogen synthase, the result of which is to reduce the rate of conversion of glucose to glycogen, giving rise to elevated blood glucose levels. This function of GSK-3 is controlled by insulin. Binding of insulin to its receptor leads indirectly to the activation of AKT and subsequent inhibitory Ser9 phosphorylation of GSK-3.

These results and observations suggest that modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral schlerosis, stroke, Huntington's disease, peripheral neuropathies, traumatic brain injury, spinal cord trauma, and vascular dementias.

Compounds that inhibit GSK-3 may also have utility in the treatment of diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma. Inhibition of GSK-3 has also been shown to downregulate PD-1 in T-reg cells, enhancing viral clearance in vivo (*Immunity*, Volume 44, Issue 2, 16 Feb. 2016).

Recent reviews on the functions of GSK-3, potential therapeutic applications, and other compounds that inhibit the enzyme are listed below: Kaidanovich-Beilin O and Woodgett J R (2011) GSK-3: functional insights from cell biology and animal models. *Front. Mol. Neurosci.* 4:40. doi: 10.3389/fnmol.2011.00040; "Glycogen Synthase Kinase 3 (GSK-3) and Its Inhibitors", Martinez, Ana/Castro, Ana/ Medina, Miguel (eds.), John Wiley and Sons (2006); and Gentles, R G, Hu, S. and Dubowchik, G M (2009) Recent Advances in the Discovery of GSK-3 Inhibitors and a Perspective on their Utility for the Treatment of Alzheimer's Disease. *Annual Reports in Medicinal Chemistry* 44, 3-26.

The invention provides technical advantages, for example, the compounds are novel inhibitors of GSK-3 and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders associated with GSK-3.

One aspect of the invention is a compound of formula I

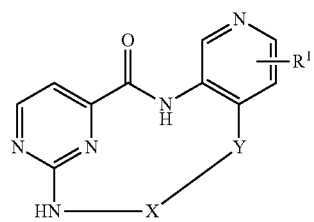

where:
R¹ is hydrogen, halo, alkyl, haloalkyl, alkoxy or haloalkoxy;
X is alkylene or alkenylene with 0-4 substituents selected from halo, alkyl, haloalkyl hydroxy, alkoxy, haloalkoxy, and $(C_{3-7})$spirocycloalkyl; and
Y is O, piperazinyl, or morpholinyl;
or a pharmaceutically acceptable salt thereof.

Another aspect of the invention is a compound of formula I where Y is O.

Another aspect of the invention is a compound of formula I where Y is piperazinyl.

Another aspect of the invention is a compound of formula I where Y is morpholinyl.

Another aspect of the invention is a compound of formula I where X is $(C_{5-7})$-alkylene.

Another aspect of the invention is a compound of formula I where X is $(C_{5-6})$-alkenylene.

For a compound of formula I, the scope of any instance of a variable substituent, including R¹, X, and Y, can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Alkylene" means a bidentate hydrocarbon chain with 4-8 carbons atoms in the chain. "Alkenylene" means a bidentate hydrocarbon chain with 4-8 carbons atoms in the chain with at least one double bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur.

"Spirocycloalkyl" means a spirocyclic hydrocarbon moiety occurring on a hydrocarbon chain (see structures below). The number of carbons designated includes the spirocyclic carbon in the hydrocarbon chain. For example, below is shown spirocyclopropyl which is $(C_3)$-spirocyclealkyl.

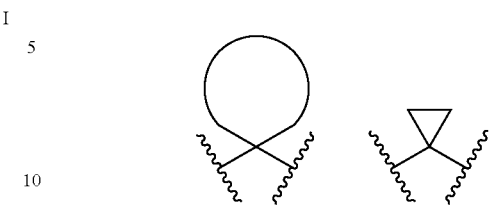

Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

The kinase assay was performed in V-bottom 384-well plates. The final assay volume was 30 µl prepared from 15 µl additions of enzyme, substrates (fluoresceinated peptide FL-KRREILSRRP[ps]ERYR-NH2 and ATP) and test compounds in assay buffer (100 mM HEPES pH 7.4, 10 mM MgCl₂, 25 mM Beta-Glycerolphosphate, 0.015% Brij35 and 0.25 mM DTT). The reaction was incubated at room temperature for 20 hours and terminated by adding 45 µl of 35 mM EDTA to each sample. The reaction mixture was analyzed on the Caliper LabChip3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 250 pM GSK3α or GSK3β, 20 uM ATP, 1.5 uM FL-KRREILSRRP[ps]ERYR-NH2, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

| Example | GSK3β/α (nM) | pTau (nM) |
|---|---|---|
| 5 | 13.5/12.1 | 1500 |
| 6 | 28.6/21.2 | 910 |
| 8 | 8.1/8.4 | 634 |
| 9 | 5.2/6.2 | 146 |
| 14 | 12.5/20.2 | 627 |
| 15 | 22.3/34.0 | 1888 |
| 17 | 1.3/3.3 | 92 |
| 18 | 3.1/6.7 | 262 |
| 23 | 0.5/0.6 | 18 |
| 24 | 2.0/3.6 | 124 |
| 26 | 3.3/4.3 | 164 |
| 28 | 14.7/17.5 | 1870 |
| 29 | 29.0/30.4 | 2656 |
| 30 | —/15.5 | 178 |
| 32 | —/2.0 | 80 |
| 34 | 1270/2000 | 9970 |
| 36 | 10.8/18.5 | 202 |
| 37 | 7.3/17.0 | 404 |
| 39 | 4.1/8.0 | 372 |
| 41 | 2.7/4.7 | 266 |
| 42 | 1.4/3.2 | 96 |
| 44 | 12.5/21.1 | 1639 |

Pharmaceutical Compositions and Methods of Treatment

Compounds of formula I can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment for modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral sclerosis, stroke, Huntington's disease, peripheral neuropathies, traumatic brain injury, spinal cord trauma, and vascular dementias, which comprises administering to a patient a therapeutically affective amount of a compound of formula I.

Another aspect of the invention is a method for the treatment for diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma, which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is the use of a compound of formula I in the manufacture of a medicament for the treatment of Alzheimer's disease.

"Patient" means a person suitable for therapy as understood by practitioners in the field of affective disorders, neurodegenerative disorders, psychiatric disorders, cancer, metabolic disorders, or inflammatory disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not Intermediate 1

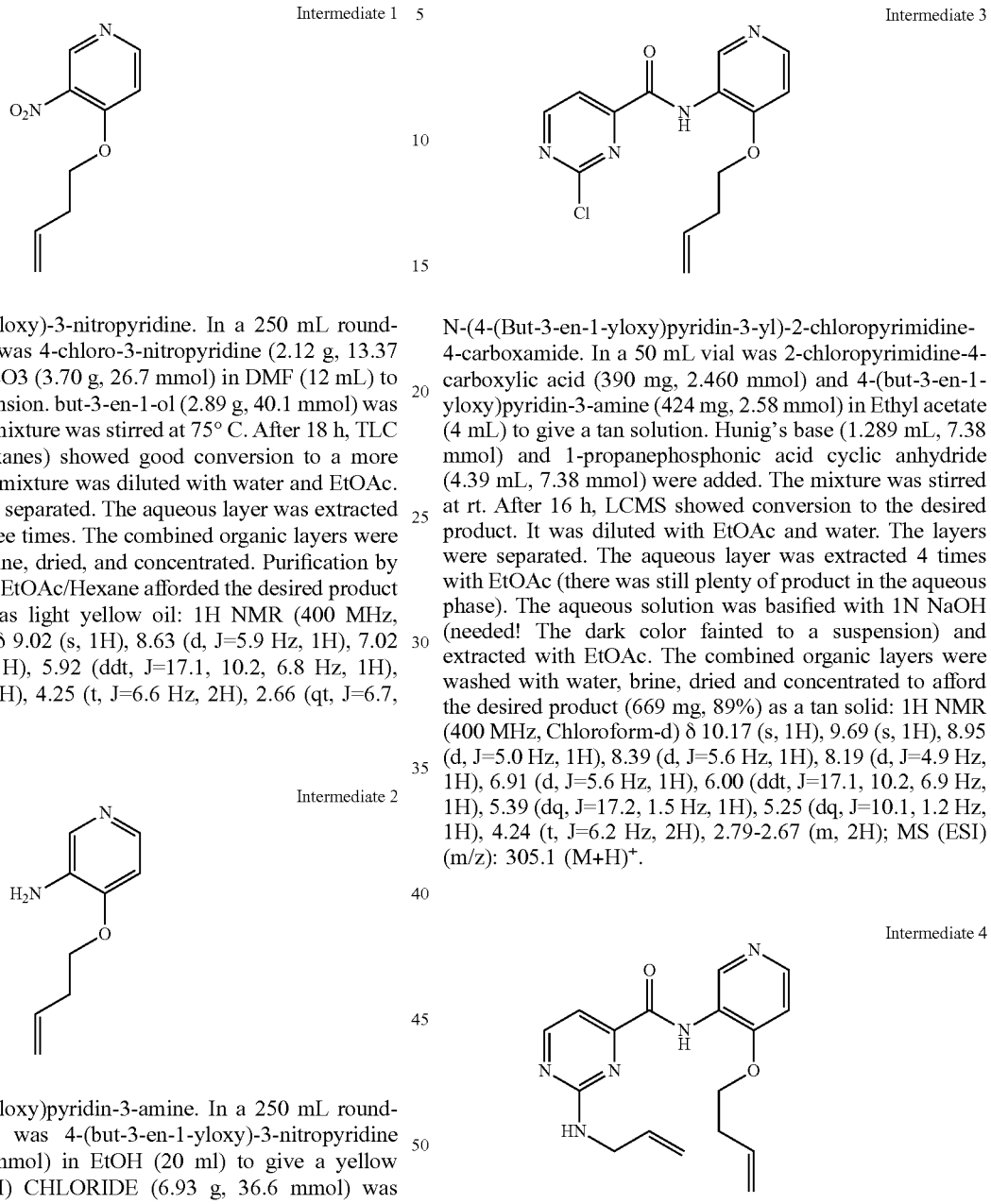

Intermediate 3

Intermediate 2

Intermediate 4

4-(But-3-en-1-yloxy)-3-nitropyridine. In a 250 mL round-bottomed flask was 4-chloro-3-nitropyridine (2.12 g, 13.37 mmol) and K2CO3 (3.70 g, 26.7 mmol) in DMF (12 mL) to give a tan suspension. but-3-en-1-ol (2.89 g, 40.1 mmol) was added, and the mixture was stirred at 75° C. After 18 h, TLC (1/1 EtOAc/hexanes) showed good conversion to a more polar spot. The mixture was diluted with water and EtOAc. The layers were separated. The aqueous layer was extracted with EtOAc three times. The combined organic layers were washed with brine, dried, and concentrated. Purification by FCC up to 80% EtOAc/Hexane afforded the desired product (1.43 g, 55%) as light yellow oil: 1H NMR (400 MHz, Chloroform-d) δ 9.02 (s, 1H), 8.63 (d, J=5.9 Hz, 1H), 7.02 (d, J=5.9 Hz, 1H), 5.92 (ddt, J=17.1, 10.2, 6.8 Hz, 1H), 5.31-5.13 (m, 2H), 4.25 (t, J=6.6 Hz, 2H), 2.66 (qt, J=6.7, 1.3 Hz, 2H).

4-(But-3-en-1-yloxy)pyridin-3-amine. In a 250 mL round-bottomed flask was 4-(but-3-en-1-yloxy)-3-nitropyridine (1.42 g, 7.31 mmol) in EtOH (20 ml) to give a yellow solution. TIN(II) CHLORIDE (6.93 g, 36.6 mmol) was added, and the mixture was heated at 70° C. under nitrogen. After 3 h, TLC indicated no starting material. The reaction mixture was cooled to r.t. Most EtOH was evaporated and the residue was diluted with EtOAc. Aqueous NaHCO3 was added to adjust pH around 7-8. The suspension was carefully filtered (through a plug of celite) and washed with EtOAc. The clear bilayer solution was separated. The organic layer was washed with brine, dried with Na2SO4, and concentrated to the desired product (1.18 g, 98%) as a light tan solid/oil: 1H NMR (400 MHz, Chloroform-d) δ 8.01 (s, 1H), 7.96 (d, J=5.4 Hz, 1H), 6.70 (d, J=5.5 Hz, 1H), 5.90 (ddt, J=17.1, 10.3, 6.7 Hz, 1H), 5.26-5.09 (m, 2H), 4.11 (t, J=6.6 Hz, 2H), 3.80 (s, 2H), 2.61 (dtd, J=6.6, 5.1, 1.4 Hz, 2H). MS (ESI) (m/z): 264 (M+H)+; $^1$H NMR (400 MHz, CDCl3) δ 9.41 (s, 1H), 8.58 (s, 1H), 8.52 (d, J=5.1 Hz, 1H), 8.29 (d, J=5.6 Hz, 1H), 7.75 (s, 1H), 7.63 (dd, J=5.1, 1.4 Hz, 1H), 6.86 (d, J=5.6 Hz, 1H), 3.97 (s, 3H).

N-(4-(But-3-en-1-yloxy)pyridin-3-yl)-2-chloropyrimidine-4-carboxamide. In a 50 mL vial was 2-chloropyrimidine-4-carboxylic acid (390 mg, 2.460 mmol) and 4-(but-3-en-1-yloxy)pyridin-3-amine (424 mg, 2.58 mmol) in Ethyl acetate (4 mL) to give a tan solution. Hunig's base (1.289 mL, 7.38 mmol) and 1-propanephosphonic acid cyclic anhydride (4.39 mL, 7.38 mmol) were added. The mixture was stirred at rt. After 16 h, LCMS showed conversion to the desired product. It was diluted with EtOAc and water. The layers were separated. The aqueous layer was extracted 4 times with EtOAc (there was still plenty of product in the aqueous phase). The aqueous solution was basified with 1N NaOH (needed! The dark color fainted to a suspension) and extracted with EtOAc. The combined organic layers were washed with water, brine, dried and concentrated to afford the desired product (669 mg, 89%) as a tan solid: 1H NMR (400 MHz, Chloroform-d) δ 10.17 (s, 1H), 9.69 (s, 1H), 8.95 (d, J=5.0 Hz, 1H), 8.39 (d, J=5.6 Hz, 1H), 8.19 (d, J=4.9 Hz, 1H), 6.91 (d, J=5.6 Hz, 1H), 6.00 (ddt, J=17.1, 10.2, 6.9 Hz, 1H), 5.39 (dq, J=17.2, 1.5 Hz, 1H), 5.25 (dq, J=10.1, 1.2 Hz, 1H), 4.24 (t, J=6.2 Hz, 2H), 2.79-2.67 (m, 2H); MS (ESI) (m/z): 305.1 (M+H)+.

2-(Allylamino)-N-(4-(but-3-en-1-yloxy)pyridin-3-yl)pyrimidine-4-carboxamide. In a 2 mL vial was N-(4-(but-3-en-1-yloxy)pyridin-3-yl)-2-chloropyrimidine-4-carboxamide (82.1 mg, 0.269 mmol) and prop-2-en-1-amine (30.8 mg, 0.539 mmol) in NMP (0.5 mL) to give a tan solution. Hunig'sBase (0.141 mL, 0.808 mmol) was added. The mixture was heated at 100° C. for 2 h. LCMS showed complete conversion to the desired product. The mixture was diluted with water and EtOAc. The layers were separated. The organic layer was washed with brine, dried and concentrated to a tan oil/solid. Purification by FCC up to 8% MeOH/CH2Cl2 afforded the desired product (72.1 mg, 82%) as a white solid: 1H NMR (400 MHz, Chloroform-d) δ 10.25 (s, 1H), 9.71 (s, 1H), 8.55 (d, J=4.9 Hz, 1H), 8.31

(d, J=5.5 Hz, 1H), 7.43 (d, J=4.8 Hz, 1H), 6.85 (d, J=5.5 Hz, 1H), 6.09-5.87 (m, 2H), 5.78 (s, 1H), 5.38-5.10 (m, 4H), 4.24-4.11 (m, 4H), 2.67 (qt, J=6.7, 1.5 Hz, 2H); MS (ESI) (m/z): 326.2 (M+H)+.

Example 5

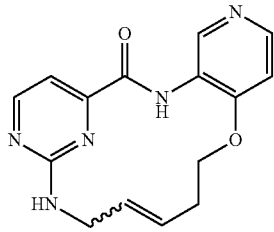 [SMILES: O=C1Nc2cnccc2OCCC=CCNc2nccc1n2]

5-Oxa-3,11-diaza-1(4,2)-pyrimidina-4(3,4)-pyridinacycloundecaphan-8-en-2-one. A solution of 2-(allylamino)-N-(4-(but-3-en-1-yloxy)pyridin-3-yl)pyrimidine-4-carboxamide (29.6 mg, 0.091 mmol), ClCH2CH2Cl (20 mL) in a 50 mL of three neck flask was degassed by a flow of N2 for 7 min. Zhan 1B catalyst (33.4 mg, 0.045 mmol) was added and the resulting greenish solution was further degassed for 4 min. It was then heated at 70° C. for 2 h. TLC showed complete conversion to a much polar spot. All volatiles were removed. The residue was subjected to purification by FCC up to 10% MeOH/CH2Cl2 to afford the desired product (9.3 mg, 34%) as a greenwish solid. 1H NMR indicated a ratio of 0.27/0.73 cis/trans isomers (unclear which was more): 1H NMR (400 MHz, Chloroform-d) δ 11.40 (s, 0.3H), 10.64 (s, 0.7H), 9.62 (s, 0.7H), 9.53 (s, 0.3H), 8.56 (dd, J=11.2, 4.8 Hz, 1H), 8.32 (dd, J=5.4, 4.0 Hz, 1H), 7.41 (dd, J=4.8, 2.6 Hz, 1H), 6.82 (dd, J=14.9, 5.4 Hz, 1H), 5.93-5.44 (m, 3H), 4.19 (t, J=5.7 Hz, 2H), 4.06 (dt, J=4.9, 2.4 Hz, 2H), 2.67 (q, J=6.4, 5.9 Hz, 2H); LCMS and analytical HPLC were also obtained (LCMS showed one peak but HPLC showed two overlapping peaks): MS (ESI) (m/z): 298.1 (M+H)+.

Example 6

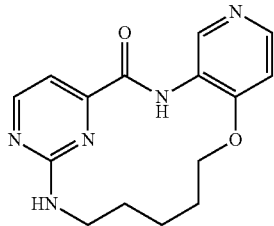 [SMILES: O=C1Nc2cnccc2OCCCCCNc2nccc1n2]

5-Oxa-3,11-diaza-1(4,2)-pyrimidina-4(3,4)-pyridinacycloundecaphan-2-one. In a 100 mL round-bottomed flask was example 1 (8 mg, 0.027 mmol) and Pd/C (5.73 mg, 5.38 μmop in MeOH (1 mL) to give a black suspension. The mixture was stirred under 1 atom hydrogen for 2 h. LCMS showed good conversion but some sm was present. After 4 h, the mixture was filtered and concentrated. The residue was purified by prep-HPLC to afford the desired product (2.7 mg, 34%): 1H NMR (500 MHz, Methanol-d4) δ 11.34 (s, 1H), 9.43 (s, 1H), 8.50 (d, J=4.9 Hz, 1H), 8.24 (d, J=5.8 Hz, 1H), 7.58 (s, 1H), 7.25 (d, J=4.8 Hz, 1H), 7.06 (d, J=5.7 Hz, 1H), 4.29 (t, J=5.3 Hz, 2H), 3.41-3.34 (m, 2H), 2.11 (ddd, J=12.2, 9.9, 6.2 Hz, 2H), 2.01 (q, J=4.1, 3.3 Hz, 2H), 1.75 (ddd, J=12.8, 8.9, 6.2 Hz, 2H). MS (ESI) (m/z): 292 (M+H)+; 1H NMR (400 MHz, MeOD) δ 9.58 (s, 1H), 8.62 (dd, J=5.2, 0.6 Hz, 1H), 8.32 (d, J=5.3 Hz, 1H), 7.92 (dd, J=1.5, 0.6 Hz, 1H), 7.83 (dd, J=5.2, 1.5 Hz, 1H), 7.46 (d, J=5.2 Hz, 1H), 1.69 (s, 6H); MS (ESI) (m/z): 300.2 (M+H)+.

Intermediate 7

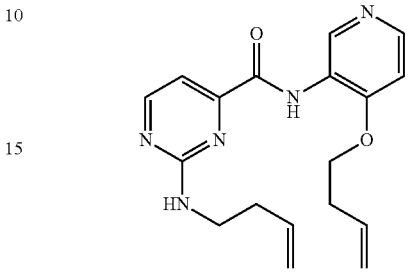

2-(But-3-en-1-ylamino)-N-(4-(but-3-en-1-yloxy)pyridin-3-yl)pyrimidine-4-carboxamide. In a 2 mL vial was N-(4-(but-3-en-1-yloxy)pyridin-3-yl)-2-chloropyrimidine-4-carboxamide (90.5 mg, 0.297 mmol) and but-3-en-1-amine (42.2 mg, 0.594 mmol) in NMP (0.5 mL) to give a tan solution. Hunig's base (0.156 mL, 0.891 mmol) was added. The mixture was heated at 100° C. for 2 h. LCMS showed complete conversion. The mixture was diluted with water and EtOAc. The layers were separated. The organic layer was washed with brine, dried and concentrated to a tan oil/solid. Purification by FCC up to 8% MeOH afforded the desired product (77.2 mg, 77%) as a white solid: 1H NMR (400 MHz, Chloroform-d) δ 10.24 (s, 1H), 9.71 (s, 1H), 8.54 (d, J=4.8 Hz, 1H), 8.31 (d, J=5.5 Hz, 1H), 7.41 (d, J=4.9 Hz, 1H), 6.85 (d, J=5.5 Hz, 1H), 6.03-5.79 (m, 2H), 5.46 (s, 1H), 5.29-5.11 (m, 4H), 4.19 (t, J=6.7 Hz, 2H), 3.58 (td, J=6.6, 5.5 Hz, 2H), 2.67 (ddt, J=8.1, 6.7, 3.3 Hz, 2H), 2.49-2.37 (m, 2H); MS (ESI) (m/z): 340.3 (M+H)+.

Example 8

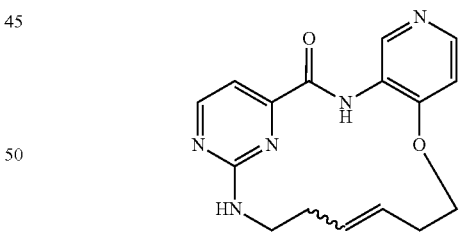

5-Oxa-3,12-diaza-1(4,2)-pyrimidina-4(3,4)-pyridinacyclododecaphan-8-en-2-one. A solution of 2-(but-3-en-1-ylamino)-N-(4-(but-3-en-1-yloxy)pyridin-3-yl)pyrimidine-4-carboxamide (29.1 mg, 0.086 mmol), ClCH2CH2Cl (20 mL) in a 50 mL of three neck flask was degassed by a flow of N2 for 7 min. Zhan 1B catalyst (31.5 mg, 0.043 mmol) was added and the resulting greenish solution was further degassed for 4 min. It was then heated at 70° C. for 2 h. TLC showed showed complete conversion to a slightly more polar spot. All volatiles were removed. The residue was purified by FCC up to 10% MeOH/CH2Cl2 to afford the desired product (12.3 mg, 46%) as a greenwish solid: 1H NMR indicated exactly 1/1 ratio of the cis/trans isomers: 1H NMR (400 MHz, Chloroform-d) δ 10.51 (s, 0.5H), 10.25 (s, 0.5H), 9.63 (s, 0.5H), 9.49 (s, 0.5H), 8.53 (dd, J=10.8, 4.8 Hz, 1H), 8.33 (d, J=5.5 Hz, 1H), 7.39 (dd, J=14.6, 4.8 Hz, 1H), 6.84 (dd, J=8.7, 5.5 Hz, 1H), 5.91 (dt, J=14.7, 7.3 Hz, 0.5H), 5.80 (t, J=6.5 Hz, 0.5H), 5.67-5.48 (m, 2H), 4.14 (dt, J=20.1, 5.1 Hz, 2H), 3.70 (tt, J=7.5, 4.0 Hz, 1H), 3.54 (ddd, J=10.4, 8.3, 4.1 Hz, 1H), 2.71-2.58 (m, 2H), 2.53 (q, J=6.0 Hz, 1H), 2.39 (dt, J=10.8, 5.5 Hz, 1H). LCMS and analytical HPLC were also obtained. MS (ESI) (m/z): 312.1 (M+H)⁺.

Example 9

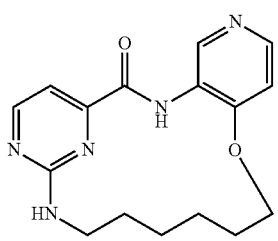 [SMILES: O=C1Nc2cnccc2OCCCCCCNc2nccc1n2]

5-Oxa-3,12-diaza-1(4,2)-pyrimidina-4(3,4)-pyridinacyclododecaphan-2-one. In a 100 mL round-bottomed flask was example 8 (11 mg, 0.035 mmol) and Pd/C (7.52 mg, 7.07 μmop in MeOH (1 mL) to give a black suspension. The mixture was stirred under 1 atom hydrogen for 4 h. The mixture was filtered and concentrated. The residue was purified by prep-HPLC to afford the desired product (1.5 mg, 14%): 1H NMR (500 MHz, DMSO-d6) δ 10.50 (s, 1H), 9.40 (s, 1H), 8.59 (d, J=4.6 Hz, 1H), 8.29 (d, J=5.4 Hz, 1H), 7.87 (t, J=6.4 Hz, 1H), 7.19 (d, J=4.7 Hz, 1H), 7.15 (d, J=5.5 Hz, 1H), 4.16 (t, J=4.9 Hz, 2H), 1.83 (d, J=8.9 Hz, 2H), 1.65 (dd, J=29.8, 15.5 Hz, 4H), 1.47 (d, J=6.4 Hz, 2H) (missing two protones: likely buried in 3.35 ppm peak); MS (ESI) (m/z): 314.2 (M+H)⁺.

2,4-Difluoro-5-nitropyridine. Sledeski, A. W.; Kubiak, G. G.; O'Brien, M. K.; Powers, M. R.; Powner, T. H.; Truesdale, L. K. *J. Org. Chem.* 2000, 65, 8114-8118. In a 250 mL round-bottomed flask was 2,4-dichloro-5-nitropyridine (4.27 g, 22.13 mmol), POTASSIUM FLUORIDE (3.86 g, 66.4 mmol), and 18C6 (0.936 g, 3.54 mmol) in NMP (15 mL) to give a tan suspension. The mixture was heated at 100° C. under nitrogen for 3 h. LCMS showed complete conversion to a new peak. The mixture was then partitioned between water and ether (with some hexane: better for getting rid of NMP). The organic layer was washed with water, brine, dried and concentrated to a tan oil. It became solid (2.8 g, 79%) when cooled in frige. The material was used as is.

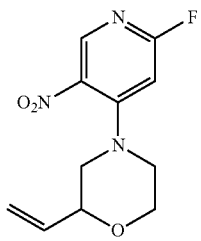

Intermediate 10

4-(2-Fluoro-5-nitropyridin-4-yl)-2-vinylmorpholine. In a 50 mL round-bottomed flask vial was 2,4-difluoro-5-nitropyridine (263.4 mg, 1.645 mmol) in tetrahydrofuran (8 mL) to give a tan solution. After cooling to −40° C., 2-vinylmorpholine hydrochloride (246 mg, 1.645 mmol) was added, followed by Et3N (0.688 mL, 4.94 mmol). The cloudy tan mixture was stirred at 31 40° C.-0° C. for 5 h. TLC (1/2 EtOAc/hexane) showed little SM and one major more polar spot. The mixture was concentrated, and the residue was purified by FCC up to 60% EtOAc/hexane to afford the desired product (348 mg, 84%) as a yellow oil: 1H NMR (400 MHz, Chloroform-d) δ 8.55 (s, 1H), 6.44 (s, 1H), 6.03-5.88 (m, 1H), 5.38-5.28 (m, 1H), 5.28-5.17 (m, 1H), 3.98-3.85 (m, 4H), 3.80 (ddd, J=11.4, 10.6, 2.8 Hz, 1H), 3.53 (ddd, J=12.8, 10.6, 3.5 Hz, 1H), 2.95 (dtd, J=12.9, 2.6, 0.9 Hz, 1H); 19F NMR (376 MHz, Chloroform-d) δ −61.65.

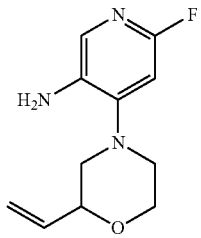

Intermediate 11

6-Fluoro-4-(2-vinylmorpholino)pyridin-3-amine. In a 250 mL round-bottomed flask was 4-(2-fluoro-5-nitropyridin-4-yl)-2-vinylmorpholine (348 mg, 1.374 mmol) in EtOH (8 ml) to give a yellow solution. TIN(II) CHLORIDE (1303 mg, 6.87 mmol) was added, and the mixture was heated at 70° C. under nitrogen. After 3 h, TLC indicated no starting material. Cooled to r.t. Most EtOH was evaporated and the residue was diluted with EtOAc. Aqueous NaHCO3 was added to adjust pH around 7-8. The suspension was carefully filtered (through a plug of celite) and washed with EtOAc. The clear bilayer solution was separated. The organic layer was washed with brine, dried with Na2SO4, and concentrated to the desired product (304 mg, 99%) as a light tan solid/oil: 1H NMR (400 MHz, Chloroform-d) δ 7.58 (s, 1H), 6.41 (d, J=1.4 Hz, 1H), 5.53 (ddd, J=17.6, 10.4, 7.3 Hz, 1H), 5.18-5.09 (m, 2H), 3.95-3.67 (m, 6H), 3.55 (td, J=8.6, 3.0 Hz, 1H), 3.31 (dt, J=12.3, 3.4 Hz, 1H), 2.66-2.57 (m, 1H); 19F NMR (376 MHz, Chloroform-d) δ −78.87.

Intermediate 12

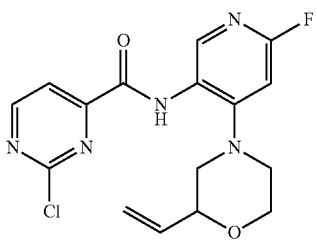

2-Chloro-N-(6-fluoro-4-(2-vinylmorpholino)pyridin-3-yl)pyrimidine-4-carboxamide. In a 100 mL flask was 2-chloropyrimidine-4-carboxylic acid (216 mg, 1.362 mmol) and 6-fluoro-4-(2-vinylmorpholino)pyridin-3-amine (304 mg, 1.362 mmol) in Ethyl acetate (3 mL) to give a tan solution. Hunig's base (0.713 mL, 4.09 mmol) and 1-propanephosphonic acid cyclic anhydride (2.432 mL, 4.09 mmol) were added. The mixture was stirred at rt over the weekend for 66 h. LCMS showed conversion to the desired product. The mixture was basified with 1 N NaOH and diluted with EtOAc and water. The layers were separated. The aqueous layer was extracted with EtOAc. The combined organic layers were washed with water, brine, dried and concentrated to afford the desired product (459 mg, 93%) as a tan oil/solid: 1H NMR (400 MHz, Chloroform-d) δ 10.51 (s, 1H), 9.24 (d, J=0.7 Hz, 1H), 8.93 (d, J=4.9 Hz, 1H), 8.13 (d, J=4.9 Hz, 1H), 6.64 (d, J=1.9 Hz, 1H), 5.51 (ddd, J=17.8, 10.3, 7.7 Hz, 1H), 5.19-5.09 (m, 2H), 4.09-3.96 (m, 3H), 3.75 (td, J=7.8, 2.9 Hz, 1H), 3.67 (dd, J=11.2, 8.0 Hz, 1H), 3.11 (dt, J=12.1, 3.1 Hz, 1H), 2.82 (dd, J=12.2, 9.1, 3.1 Hz, 1H); 19F NMR (376 MHz, Chloroform-d) δ −69.23; MS (ESI) (m/z): 364.2 (M+H)$^+$.

Intermediate 13

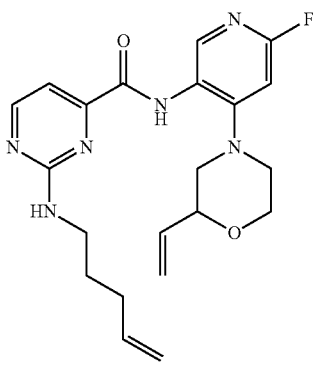

N-(6-Fluoro-4-(2-vinylmorpholino)pyridin-3-yl)-2-(pent-4-en-1-ylamino)pyrimidine-4-carboxamide. In a 2 mL vial was 2-chloro-N-(6-fluoro-4-(2-vinylmorpholino)pyridin-3-yl)pyrimidine-4-carboxamide (58.7 mg, 0.161 mmol) and pent-4-en-1-amine (27.5 mg, 0.323 mmol) in NMP (0.3 mL) to give a tan solution. Hunig's base (0.085 mL, 0.484 mmol) was added. The mixture was heated at 100° C. for 2 h. LCMS showed complete conversion to the desired product. The mixture was diluted with water and EtOAc. The layers were separated. The organic layer was washed with brine, dried and concentrated to a tan oil/solid. Purification by FCC up to 70% EtOAc/hexane afforded the desired product (48 mg, 72%) as a light green oil: 1H NMR (400 MHz, Chloroform-d) δ 10.30 (s, 1H), 9.30 (s, 1H), 8.56 (d, J=4.9 Hz, 1H), 7.43 (d, J=4.8 Hz, 1H), 6.75-6.62 (m, 1H), 5.85 (ddt, J=16.9, 10.2, 6.6 Hz, 1H), 5.55 (ddd, J=17.8, 10.4, 7.7 Hz, 2H), 5.24-5.15 (m, 2H), 5.12-4.98 (m, 2H), 4.07-3.85 (m, 3H), 3.77 (td, J=7.9, 3.2 Hz, 1H), 3.73-3.44 (m, 3H), 3.23-3.04 (m, 1H), 2.82 (ddd, J=12.3, 9.0, 3.4 Hz, 1H), 2.28-2.16 (m, 2H), 1.81 (p, J=7.1 Hz, 2H); 19F NMR (376 MHz, Chloroform-d) δ −70.16; MS (ESI) (m/z): 413.3 (M+H)$^+$.

Example 14

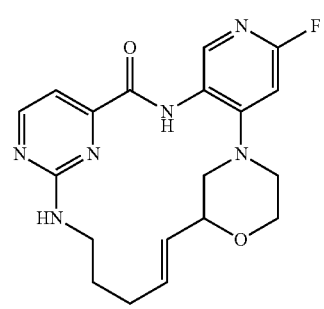 [SMILES: O=C1Nc2cnc(F)cc2N2CCOC(/C=C/CCCNc3nccc1n3)C2]

(E)-2$^6$-Fluoro-3,6-diaza-1(4,2)-morpholina-5(4,2)-pyrimidina-2(4,3)-pyridinacycloundecaphan-10-en-4-one. A solution of N-(6-fluoro-4-(2-vinylmorpholino)pyridin-3-yl)-2-(pent-4-en-1-ylamino)pyrimidine-4-carboxamide (46 mg, 0.112 mmol), ClCH2CH2Cl (20 mL) in a 50 mL of three neck flask was degassed by a flow of N2 for 7 min. Zhan 1B catalyst (32.7 mg, 0.045 mmol) was added and the resulting greenish solution was further degassed for 4 min. It was then heated at 70° C. for 2 h. TLC showed good conversion to a more polar spot (with may be a trace SM). All volatiles were removed. The residue was subjected to purification by FCC up to 80% EtOAc/hexane to afford the desired product (19.8 mg, 46%) as a tan solid. 1H NMR indicated a ratio of 0.27/0.73 cis/trans isomers (unclear which was more): 1H NMR (400 MHz, Chloroform-d) δ 9.83 (s, 1H), 9.17 (s, 1H), 8.52 (d, J=4.8 Hz, 1H), 7.41 (d, J=4.8 Hz, 1H), 6.65 (d, J=1.2 Hz, 1H), 6.03 (dddd, J=15.7, 6.7, 5.0, 1.5 Hz, 1H), 5.92 (ddt, J=15.7, 4.3, 1.3 Hz, 1H), 5.60 (dd, J=9.5, 4.7 Hz, 1H), 4.12-4.00 (m, 1H), 3.97-3.82 (m, 4H), 3.82-3.67 (m, 2H), 3.28-3.09 (m, 2H), 2.42-2.26 (m, 1H), 2.26-2.10 (m, 1H), 1.86 (tdd, J=13.0, 5.1, 2.5 Hz, 1H), 1.68 (dtd, J=13.3, 6.5, 3.3 Hz, 1H); 19F NMR (376 MHz, Chloroform-d) δ −70.90; MS (ESI) (m/z): 385.3 (M+H)$^+$.

Example 15

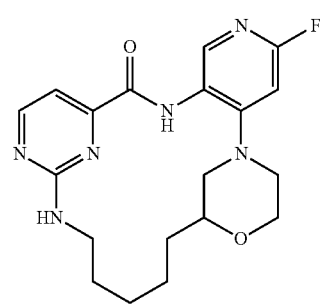 [SMILES: O=C1Nc2cnc(F)cc2N2CCOC(CCCCCNc3nccc1n3)C2]

2⁶-Fluoro-3,6-diaza-1(4,2)-morphohna-5(4,2)-pyrimidina-2(4,3)-pyridinacycloundecaphan-4-one. In a 100 mL round-bottomed flask was example 14 (7.3 mg, 0.019 mmol) and Pd/C (4.04 mg, 3.80 μmop in MeOH (1 mL) to give a black suspension. The mixture was stirred under 1 atom hydrogen for 22 h. LCMS showed complete conversion. The mixture was filtered and concentrated to the desired product (6.3 mg, 86%) as an off-white solid: 1H NMR (400 MHz, Chloroform-d) δ 9.95 (s, 1H), 9.02 (s, 1H), 8.54 (d, J=4.8 Hz, 1H), 7.41 (d, J=4.8 Hz, 1H), 6.66 (d, J=1.1 Hz, 1H), 5.65 (t, J=7.0 Hz, 1H), 4.02 (dd, J=11.7, 3.1 Hz, 1H), 3.71-3.40 (m, 5H), 3.33 (dt, J=11.4, 3.3 Hz, 1H), 2.99-2.91 (m, 1H), 2.46-2.30 (m, 1H), 1.67-1.46 (m, 6H), 1.35-1.24 (m, 2H); 19F NMR (376 MHz, Chloroform-d) δ −70.52; MS (ESI) (m/z): 387.3 (M+H)⁺.

Intermediate 16

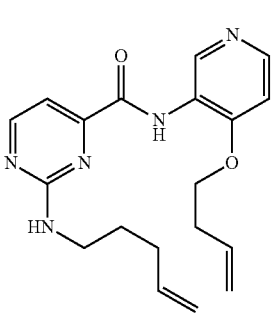

N-(4-(But-3-en-1-yloxy)pyridin-3-yl)-2-(pent-4-en-1-ylamino)pyrimidine-4-carboxamide. In a 2 mL vial was N-(4-(but-3-en-1-yloxy)pyridin-3-yl)-2-chloropyrimidine-4-carboxamide (115.9 mg, 0.380 mmol) and pent-4-en-1-amine (64.8 mg, 0.761 mmol) in NMP (0.7 mL) to give a tan solution. Hunig'sBase (0.199 mL, 1.141 mmol) was added. The mixture was heated at 100° C. for 2 h. LCMS showed complete conversion to the desired product. The mixture was diluted with water and EtOAc. The layers were separated. The organic layer was washed with brine, dried and concentrated to a tan oil/solid. Purification by FCC up to 8% MeOH afforded the desired product (118 mg, 88%) as an off-white solid: 1H NMR (400 MHz, Chloroform-d) δ 10.19 (s, 1H), 9.66 (s, 1H), 8.49 (d, J=4.8 Hz, 1H), 8.27 (d, J=5.5 Hz, 1H), 7.36 (d, J=4.8 Hz, 1H), 6.83 (d, J=5.5 Hz, 1H), 5.84 (tdt, J=16.9, 10.2, 7.1 Hz, 2H), 5.20 (d, J=17.2 Hz, 1H), 5.16-5.10 (m, 1H), 5.03 (dq, J=17.1, 1.7 Hz, 1H), 4.97 (dq, J=10.2, 1.5 Hz, 1H), 4.17 (t, J=6.7 Hz, 2H), 3.49 (q, J=6.6 Hz, 2H), 2.67-2.58 (m, 2H), 2.44 (s, 1H), 2.21-2.12 (m, 2H), 1.74 (p, J=7.1 Hz, 2H); MS (ESI) (m/z): 354.2 (M+H)⁺.

Example 17

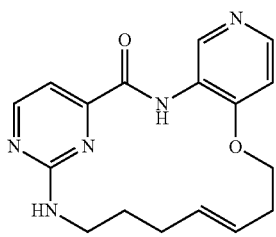 [SMILES: O=C1Nc2cnccc2OCC/C=C/CCCNc2nccc1n2]

(E)-5-Oxa-3,13-diaza-1(4,2)-pyrimidina-4(3,4)-pyridinacyclotridecaphan-8-en-2-one. A solution of N-(4-(but-3-en-1-yloxy)pyridin-3-yl)-2-(pent-4-en-1-ylamino)pyrimidine-4-carboxamide (118 mg, 0.334 mmol), ClCH2CH2Cl (60 mL) in a 50 mL of three neck flask was degassed by a flow of N2 for 7 min. Zhan 1B catalyst (73.5 mg, 0.100 mmol) was added and the resulting greenish solution was further degassed for 4 min. It was then heated at 70° C. for 2 h. TLC showed showed complete conversion to a slightly more polar spot. All volatiles were removed. The residue was purified by FCC up to 10% MeOH/CH2Cl2 to afford the desired product (25.1 mg, 23%) as a tan solid. 1H NMR was difficult to distingush between the isomers; MS (ESI) (m/z): 326.1 (M+H)⁺.

Example 18

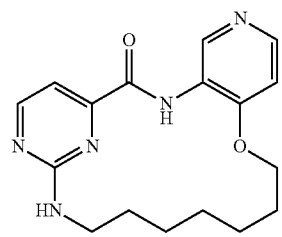 [SMILES: O=C1Nc2cnccc2OCCCCCCCNc2nccc1n2]

5-Oxa-3,13-diaza-1(4,2)-pyrimidina-4(3,4)-pyridinacyclotridecaphan-2-one. In a 50 mL round-bottomed flask was example 17 (3.9 mg, 0.012 mmol) and Pd/C (6.38 mg, 5.99 μmop in MeOH (1 mL) to give a black suspension. The mixture was stirred under 1 atom hydrogen for 17 h. LCMS showed complete conversion. The mixture was filtered and concentrated to the desired product (2.5 mg, 51%) as a tan solid: MS (ESI) (m/z): 328.2 (M+H)⁺.

Intermediate 19

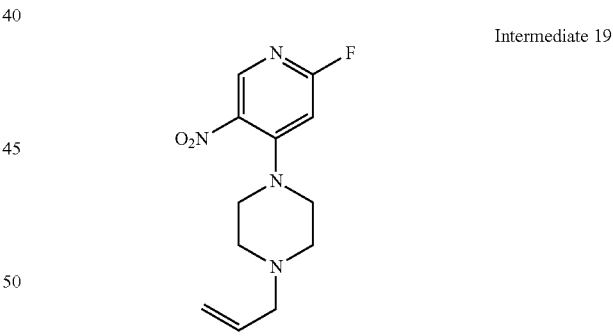

1-Allyl-4-(2-fluoro-5-nitropyridin-4-yl)piperazine. In a 250 mL round-bottomed flask vial was 2,4-difluoro-5-nitropyridine (1.035 g, 6.47 mmol) in tetrahydrofuran (30 mL) to give a tan solution. After cooling to −40° C., 1-allylpiperazine (0.905 mL, 6.47 mmol) was added, followed by Et3N (1.802 mL, 12.93 mmol). The cloudy tan mixture was stirred at −40° C.--10° C. for 3 h. TLC (1/1 EtOAc/hexane) showed one major more polar yellow spot. The mixture was concentrated, and the residue was purified by FCC up to 80% EtOAc/hexane to afford the desired product (1.4347 g, 83%) as a yellow solid: 1H NMR (400 MHz, Chloroform-d) δ 8.58 (s, 1H), 6.41 (s, 1H), 5.97-5.77 (m, 1H), 5.31-5.16 (m, 2H), 3.33-3.23 (m, 4H), 3.09 (dt, J=6.7, 1.3 Hz, 2H), 2.68-2.58 (m, 4H); 19F NMR (376 MHz, Chloroform-d) δ −62.07.

Intermediate 20

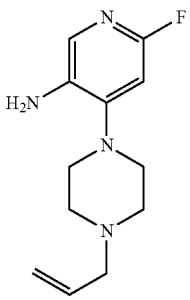

4-(4-Allylpiperazin-1-yl)-6-fluoropyridin-3-amine. In a 250 mL round-bottomed flask was 1-allyl-4-(2-fluoro-5-nitropyridin-4-yl)piperazine (1.4347 g, 5.39 mmol) in EtOH (30 ml) to give a yellow solution. TIN(II) CHLORIDE (5.11 g, 26.9 mmol) was added, and the mixture was heated at 70° C. under nitrogen for 3 h. TLC indicated no starting material. Cooled to r.t. Most EtOH was evaporated and the residue was diluted with EtOAc. Aqueous NaHCO3 was added to adjust pH around 7-8. The suspension was carefully filtered (through a plug of celite) and washed with EtOAc. The clear bilayer solution was separated. The organic layer was washed with brine, dried with Na2SO4, and concentrated to the desired product (0.718 g, 56%) as a tan oil: 1H NMR (400 MHz, Chloroform-d) δ 7.56 (d, J=1.2 Hz, 1H), 6.43 (d, J=1.4 Hz, 1H), 5.91 (ddt, J=16.8, 10.1, 6.5 Hz, 1H), 5.31-5.17 (m, 2H), 3.55 (s, 2H), 3.10 (qq, J=4.4, 2.3 Hz, 6H), 2.72-2.55 (m, 4H); 19F NMR (376 MHz, Chloroform-d) δ −78.05.

Intermediate 21

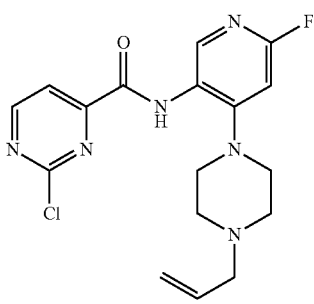

N-(4-(4-Allylpiperazin-1-yl)-6-fluoropyridin-3-yl)-2-chloropyrimidine-4-carboxamide. In a 100 mL flask was 2-chloropyrimidine-4-carboxylic acid (209 mg, 1.315 mmol) and 4-(4-allylpiperazin-1-yl)-6-fluoropyridin-3-amine (310.8 mg, 1.315 mmol) in ethyl acetate (3 mL) to give a tan solution. Hunig's base (0.689 mL, 3.95 mmol) and 1-propanephosphonic acid cyclic anhydride (2.349 mL, 3.95 mmol) were added. The mixture was stirred at rt over the weekend for 68 h. LCMS showed conversion to the desired product. The mixture was basified with 1N NaOH and diluted with EtOAc and water. The layers were separated. The aqueous layer was extracted with EtOAc. The combined organic layers were washed with water, brine, dried and concentrated to afford the desired product (413 mg, 83%) as a tan solid: 1H NMR (400 MHz, Chloroform-d) δ 10.14 (s, 1H), 9.25 (s, 1H), 8.97 (d, J=4.9 Hz, 1H), 8.19 (d, J=4.9 Hz, 1H), 6.66 (d, J=1.7 Hz, 1H), 5.99-5.87 (m, 1H), 5.33-5.21 (m, 2H), 3.18 (dt, J=6.6, 1.3 Hz, 2H), 3.14-3.08 (m, 4H), 2.83 (t, J=4.6 Hz, 4H); 19F NMR (376 MHz, Chloroform-d) δ −68.81; MS (ESI) (m/z): 377.1 (M+H)+.

Intermediate 22

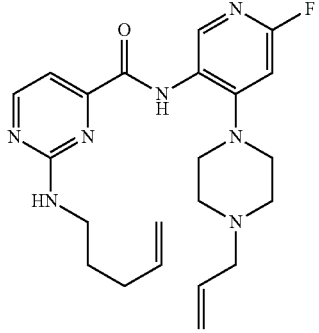

N-(4-(4-Allylpiperazin-1-yl)-6-fluoropyridin-3-yl)-2-(pent-4-en-1-ylamino)pyrimidine-4-carboxamide. In a 15 mL vial was N-(4-(4-allylpiperazin-1-yl)-6-fluoropyridin-3-yl)-2-chloropyrimidine-4-carboxamide (255 mg, 0.677 mmol) and pent-4-en-1-amine (86 mg, 1.015 mmol) in NMP (1 mL) to give a tan solution. Hunig's base (0.236 mL, 1.353 mmol) was added. The mixture was heated at 100° C. for 2 h. LCMS showed complete conversion to the desired product. The mixture was diluted with water and EtOAc. The layers were separated. The organic layer was washed with brine, dried and concentrated to a tan oil/solid. Purification by FCC up to 70% EtOAc/hexane afforded the desired product (274.8 mg, 95%) as a tan oil: 1H NMR (400 MHz, Chloroform-d) δ 9.83 (s, 1H), 9.05 (s, 1H), 8.50 (d, J=4.9 Hz, 1H), 7.35 (d, J=4.8 Hz, 1H), 6.55 (d, J=1.4 Hz, 1H), 5.90-5.50 (m, 3H), 5.24-5.12 (m, 2H), 5.06-4.94 (m, 2H), 3.55 (q, J=6.6 Hz, 2H), 3.09-2.97 (m, 6H), 2.64 (t, J=4.6 Hz, 4H), 2.23-2.13 (m, 2H), 1.76 (p, J=7.2 Hz, 2H); 19F NMR (376 MHz, Chloroform-d) δ −69.99; MS (ESI) (m/z): 426.4 (M+H)+.

Example 23

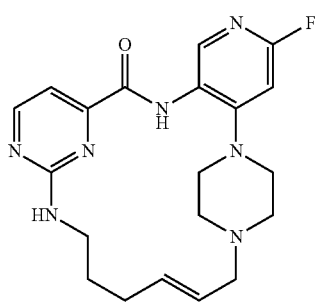 [SMILES: O=C1Nc2cnc(F)cc2N2CCN(C/C=C/CCCNc3nccc1n3)CC2]

(E)-2⁶-fluoro-3,6-diaza-5(4,2)-pyrimidina-1(1,4)-piperazina-2(4,3)-pyridinacyclododecaphan-10-en-4-one. A solution of N-(4-(4-allylpiperazin-1-yl)-6-fluoropyridin-3-yl)-2-(pent-4-en-1-ylamino)pyrimidine-4-carboxamide (240 mg, 0.564 mmol), ClCH2CH2Cl (100 mL) in a 50 mL of round-bottom flask was degassed by a flow of N2 for 5 min. Zhan 1B catalyst (83 mg, 0.113 mmol) was added and the resulting greenish solution was further degassed for 4 min. It was then heated at 70° C. for 2 h. TLC showed good conversion to a more polar spot. All volatiles were removed.

The residue was subjected to purification by FCC up to 8% MeOH/CH2Cl2 to afford the desired product (169 mg, 65%) as a tan solid: 1H NMR (500 MHz, Chloroform-d) δ 9.82 (s, 1H), 9.25 (s, 1H), 8.55 (d, J=4.7 Hz, 1H), 7.48 (d, J=4.7 Hz, 1H), 6.60 (d, J=1.7 Hz, 1H), 5.74 (br, 1H), 5.62 (br, 1H), 5.31 (br, 1H), 3.55 (s, 2H), 3.39 (d, J=7.4 Hz, 2H), 2.87 (s, 8H), 2.45-2.33 (m, 2H), 1.88 (p, J=7.0 Hz, 2H); 19F NMR (470 MHz, Chloroform-d) δ −70.02; It seems by 1H NMR that only one isomer is present (tentatively assigned as trans); MS (ESI) (m/z): 398.3 (M+H)+.

Example 24

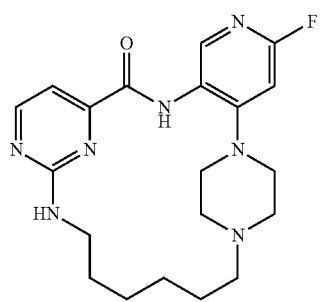 [SMILES: O=C1Nc2cnc(F)cc2N2CCN(CCCCCCNc3nccc1n3)CC2]

$2^6$-Fluoro-3,6-diaza-5(4,2)-pyrimidina-1(1,4)-piperazina-2(4,3)-pyridinacyclododecaphan-4-one. In a 50 mL round-bottomed flask was example 23 (9 mg, 0.023 mmol) and Pd/C (7.23 mg, 6.79 μmol) in MeOH (0.5 mL). The mixture was stirred under 1 atom hydrogen for 3 h. The reaction continued overnight. LCMS showed the desired as well as overreduct of one double bond. The mixture was filtered and concentrated. The residue was purified by prep-HPLC to afford the desired product (0.9 mg, 9.8%): 1H NMR (400 MHz, Methanol-d4) δ 8.87 (s, 1H), 8.54 (d, J=4.8 Hz, 1H), 7.33 (d, J=4.8 Hz, 1H), 6.83 (s, 1H), 4.63 (s, 1H), 3.59 (t, J=6.5 Hz, 2H), 3.05 (dd, J=18.7, 5.4 Hz, 8H), 2.95 (s, 2H), 1.83-1.60 (m, 8H) (missing one proton: NH); MS (ESI) (m/z): 400.3 (M+H)+.

Intermediate 25

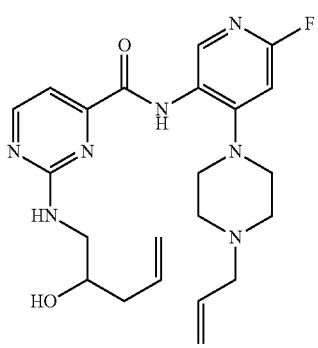

N-(4-(4-Allylpiperazin-1-yl)-6-fluoropyridin-3-yl)-2-((2-hydroxypent-4-en-1-yl)amino)pyrimidine-4-carboxamide. In a 5 mL vial was N-(4-(4-allylpiperazin-1-yl)-6-fluoropyridin-3-yl)-2-chloropyrimidine-4-carboxamide (65.4 mg, 0.174 mmol) and 1-aminopent-4-en-2-ol hydrochloride (47.8 mg, 0.347 mmol) in NMP (0.4 mL) to give a tan solution. Hunig's base (0.091 mL, 0.521 mmol) was added. The mixture was heated at 100° C. for 17 h. LCMS showed good conversion to the desired product. The mixture was diluted with water and EtOAc. The layers were separated. The organic layer was washed with brine, dried and concentrated to a tan oil/solid. Purification by FCC up to 70% EtOAc/hexane afforded the desired product (36.4 mg, 48%) as a colorless oil: 1H NMR (400 MHz, Chloroform-d) δ 9.89 (s, 1H), 9.12 (s, 1H), 8.57 (d, J=4.9 Hz, 1H), 7.45 (dd, J=5.0, 1.6 Hz, 1H), 6.60 (d, J=1.5 Hz, 1H), 5.89 (dddd, J=14.2, 13.0, 6.7, 2.5 Hz, 2H), 5.70 (s, 1H), 5.29-5.18 (m, 4H), 3.98 (tdd, J=7.8, 5.0, 3.3 Hz, 1H), 3.80 (ddd, J=13.8, 6.7, 3.3 Hz, 1H), 3.56-3.45 (m, 1H), 3.14-3.05 (m, 6H), 2.85 (s, 1H), 2.71 (t, J=4.8 Hz, 4H), 2.48-2.39 (m, 1H), 2.34 (dtt, J=14.0, 7.7, 1.2 Hz, 1H); 19F NMR (376 MHz, Chloroform-d) δ −69.82; MS (ESI) (m/z): 442.3 (M+H)+.

Example 26

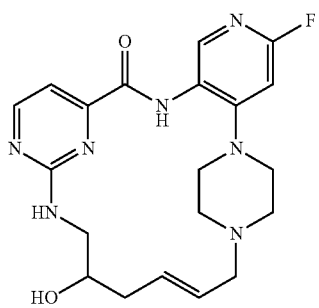 [SMILES: O=C1Nc2cnc(F)cc2N2CCN(C/C=C/CC(O)CNc3nccc1n3)CC2]

(E)-$2^6$-fluoro-8-hydroxy-3,6-diaza-5(4,2)-pyrimidina-1(1,4)-piperazina-2(4,3)-pyridinacyclododecaphan-10-en-4-one. A solution of N-(4-(4-allylpiperazin-1-yl)-6-fluoropyridin-3-yl)-2-((2-hydroxypent-4-en-1-yl) amino)pyrimidine-4-carboxamide (35.1 mg, 0.080 mmol), ClCH2CH2Cl (15 mL) in a 50 mL of round-bottom flask was degassed by a flow of N2 for 5 min. Zhan 1B catalyst (17.50 mg, 0.024 mmol) was added under nitrogen. It was then heated at 70° C. for 4 h. TLC showed a more polar major spot. All volatiles were removed. The residue was subjected to purification by FCC up to 10% MeOH/CH2Cl2 to afford the desired product (16.4 mg, 50%) as a dark solid: 1H NMR (400 MHz, Chloroform-d) δ 9.59 (s, 1H), 9.24 (s, 1H), 8.53 (d, J=4.7 Hz, 1H), 7.52 (d, J=4.6 Hz, 1H), 6.60 (d, J=1.6 Hz, 1H), 6.05 (s, 1H), 5.86-5.74 (m, 1H), 5.64 (ddd, J=14.9, 8.0, 5.0 Hz, 1H), 4.11 (s, 1H), 3.80 (ddd, J=12.5, 6.1, 3.0 Hz, 1H), 3.47-3.25 (m, 3H), 3.04-2.69 (m, 7H), 2.67-2.22 (m, 4H); 19F NMR (376 MHz, Chloroform-d) δ −70.06; MS (ESI) (m/z): 414.3 (M+H)+.

Intermediate 27

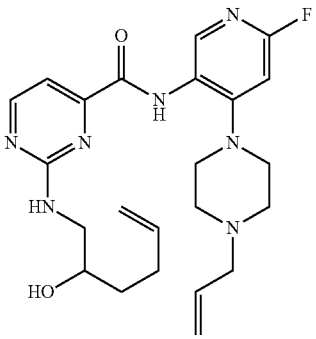

N-(4-(4-Allylpiperazin-1-yl)-6-fluoropyridin-3-yl)-2-((2-hydroxyhex-5-en-1-yl)amino)pyrimidine-4-carboxamide. In a 5 mL vial was N-(4-(4-allylpiperazin-1-yl)-6-fluoropyridin-3-yl)-2-chloropyrimidine-4-carboxamide (53.4 mg, 0.142 mmol) and 1-aminohex-5-en-2-ol hydrochloride (43.0 mg, 0.283 mmol) in NMP (0.3 mL) to give a tan solution. Hunig's base (0.074 mL, 0.425 mmol) was added. The mixture was heated at 100° C. for 17 h. LCMS showed around half conversion (by parent ion peaks: SM and product overlap), which was comformed by TLC (10% MeOH/CH2Cl2). More reagents (2 equiv/3 equiv) were added and the mixture was heated at 120° C. for 5 h. LCMS indicated a better conversion. The mixture was diluted with water and EtOAc. The layers were separated. The organic layer was washed with brine, dried and concentrated. Purification by FCC up to 70% EtOAc/hexane afforded the desired product (14 mg, 22%) as a tan oil. It was directly used in the next reaction. MS (ESI) (m/z): 456.3 (M+H)$^+$.

Example 28 and 29

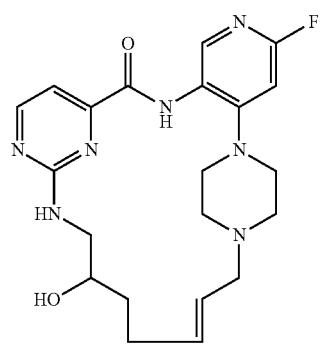

Example 28

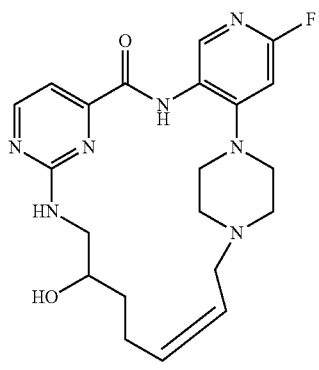

Example 29

(E)-2$^6$-fluoro-8-hydroxy-3,6-diaza-5(4,2)-pyrimidina-1(1,4)-piperazina-2(4,3)-pyridinacyclotridecaphan-11-en-4-one (28) and (Z)-2$^6$-fluoro-8-hydroxy-3,6-diaza-5(4,2)-pyrimidina-1(1,4)-piperazina-2(4,3)-pyridinacyclotridecaphan-11-en-4-one (29). A solution of N-(4-(4-allylpiperazin-1-yl)-6-fluoropyridin-3-yl)-2-((2-hydroxyhex-5-en-1-yl)amino)pyrimidine-4-carboxamide (14 mg, 0.031 mmol), ClCH2CH2Cl (6 mL) in a 50 mL of round-bottom flask was degassed by a flow of N2 for 5 min. Zhan 1B catalyst (6.77 mg, 9.22 µmol) was added under nitrogen. It was then heated at 70° C. for 3 h. TLC showed good conversion to two more polar separable spots. All volatiles were removed. The residue was subjected to purification by FCC up to 10% MeOH/CH2Cl2 to afford two separable desired products, 28 (1.7 mg, 13%) and 29 (2.9 mg, 22%), as dark oil/solids (the cis/trans assignment was arbitary). 28: 1H NMR (400 MHz, Chloroform-d) δ 10.04 (s, 1H), 9.15 (s, 1H), 8.56 (d, J=5.0 Hz, 1H), 7.48 (d, J=5.0 Hz, 1H), 6.58 (d, J=1.7 Hz, 1H), 5.84-5.68 (m, 1H), 5.61-5.42 (m, 2H), 4.06-3.91 (m, 2H), 3.63 (s, 1H), 3.24-2.27 (m, 13H), 1.79 (t, J=13.3 Hz, 2H); 19F NMR (376 MHz, Chloroform-d) δ -69.56; MS (ESI) (m/z): 428.3 (M+H)$^+$. 29: 1H NMR (400 MHz, Chloroform-d) δ 9.67 (s, 1H), 8.99 (s, 1H), 8.56 (d, J=4.9 Hz, 1H), 7.48 (d, J=4.9 Hz, 1H), 6.57 (d, J=1.4 Hz, 1H), 5.75 (d, J=6.2 Hz, 2H), 5.56 (s, 1H), 4.04 (s, 1H), 3.69 (s, 2H), 3.45-3.29 (m, 2H), 3.14-2.92 (m, 5H), 2.80 (s, 5H), 2.37-2.11 (m, 3H); 19F NMR (376 MHz, Chloroform-d) δ -69.56; MS (ESI) (m/z): 428.3 (M+H)$^+$.

Example 30

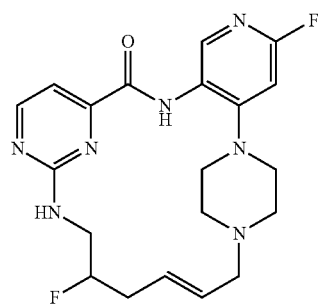 [SMILES: O=C1Nc2cnc(F)cc2N2CCN(C/C=C/CC(F)CNc3nccc1n3)CC2]

(E)-2$^{6,8}$-Difluoro-3,6-diaza-5(4,2)-pyrimidina-1(1,4)-piperazina-2(4,3)-pyridinacyclododecaphan-10-en-4-one. In a 2 mL vial was example 26 (4.0 mg, 9.67 µmol) in CH2Cl2 (0.2 mL) to give a tan solution. DAST (3.83 µl, 0.029 mmol) (one drop) was added, and the mixture was stirred at rt for 2 h. LCMS indicated there was the desired product. The mixture was diluted with MeOH, quenched with 1 drop 1 N NaOH, and was purified by prep-HPLC to afford the desired product (1.3 mg, 32%): MS (ESI) (m/z): 416.3 (M+H)$^+$.

Intermediate 31

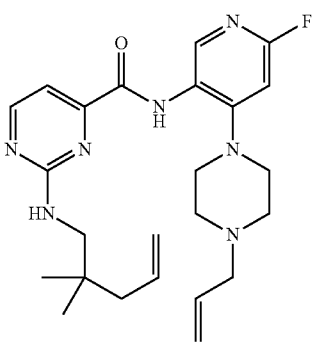

N-(4-(4-Allylpiperazin-1-yl)-6-fluoropyridin-3-yl)-2-((2,2-dimethylpent-4-en-1-yl)amino)pyrimidine-4-carboxamide.
In a 5 mL vial was N-(4-(4-allylpiperazin-1-yl)-6-fluoropyridin-3-yl)-2-chloropyrimidine-4-carboxamide (24.2 mg, 0.064 mmol) (last batch) and 2,2-dimethylpent-4-en-1-amine (14.54 mg, 0.128 mmol) in NMP (0.2 mL) to give a tan solution. Hunig's base (0.022 mL, 0.128 mmol) was added. The mixture was heated at 100° C. for 1 h. LCMS showed ⅓ conversion. The mixture was heated at 120° C. for 10 h. LCMS showed good conversion to the desired product. The mixture was diluted with water and EtOAc. The layers were separated. The organic layer was washed with brine, dried and concentrated to a tan oil/solid. Purification by FCC up to 8% MeOH/CH2Cl2 afforded the desired product (29 mg, 100%) as a tan oil. 1H NMR showed the presence of NMP. The material was used as is. 19F NMR (470 MHz, Chloroform-d) δ −69.96; MS (ESI) (m/z): 454.3 (M+H)+.

Example 32

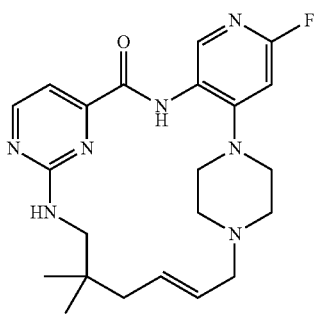 [SMILES: CC1(C)C/C=C/CN2CCN(CC2)c2cc(F)ncc2NC(=O)c2ccnc(n2)NC1]

(E)-2⁶-Fluoro-8,8-dimethyl-3,6-diaza-5(4,2)-pyrimidina-1(1,4)-piperazina-2(4,3)-pyridinacyclododecaphan-10-en-4-one. A solution of N-(4-(4-allylpiperazin-1-yl)-6-fluoropyridin-3-yl)-2-((2,2-dimethylpent-4-en-1-yl)amino)pyrimidine-4-carboxamide (29 mg, 0.064 mmol), ClCH2CH2Cl (15 mL) in a 50 mL of round-bottom flask was degassed by a flow of N2 for 5 min. Zhan 1B catalyst (14.07 mg, 0.019 mmol) was added under nitrogen. It was then heated at 70° C. for 1.5 h. TLC (9/1 CH2Cl2/MeOH) showed complete conversion to a slightly more polar spot. All volatiles were removed. The residue was subjected to purification by FCC up to 8% MeOH/CH2Cl2 to afford the desired product (9.3 mg, 34% for 2 steps) as a dark solid: 1H NMR (400 MHz, Chloroform-d) δ 9.99 (s, 1H), 9.19 (s, 1H), 8.57 (d, J=4.8 Hz, 1H), 7.46 (d, J=4.8 Hz, 1H), 6.60 (d, J=1.8 Hz, 1H), 5.79 (br, 2H), 5.40 (s, 1H), 3.47-3.32 (m, 4H), 2.98 (m, 8H), 2.28-2.19 (m, 2H), 1.13 (s, 6H); MS (ESI) (m/z): 426.3 (M+H)+.

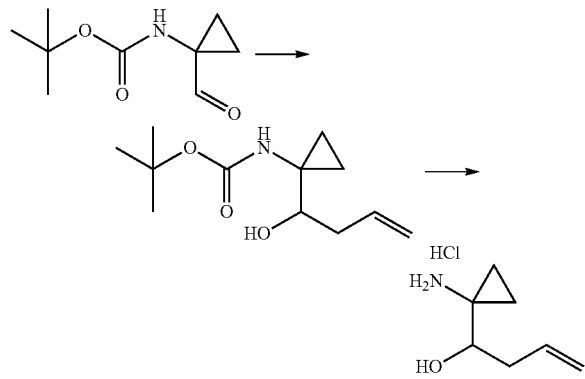

1-(1-Aminocyclopropyl)but-3-en-1-ol hydrochloride. In a 100 mL round-bottomed flask was tert-butyl (1-formylcyclopropyl)carbamate (468 mg, 2.53 mmol) in Tetrahydrofuran (8 mL) to give a colorless solution. Allylmagnesium bromide (5.05 mL, 5.05 mmol) was slowly added. The mixture was stirred at rt for 1 h and was quenched with saturated NH4Cl solution. The layers were separated. The aqueous layer was extracted with EtOAc. The combined organic layers were washed with brine, dried and concentrated to a tan oil (580 mg, 100%). Crude 1H NMR indicated the desired product: 1H NMR (400 MHz, Chloroform-d) δ 5.89 (ddt, J=17.2, 10.1, 7.1 Hz, 1H), 5.21-4.99 (m, 3H), 3.15-3.02 (m, 1H), 2.45-2.33 (m, 2H), 1.46 (s, 9H), 1.04-0.70 (m, 4H). In a 100 mL round-bottomed flask was tert-butyl (1-(1-hydroxybut-3-en-1-yl)cyclopropyl)carbamate (0.575 g, 2.53 mmol). HCl (3.80 ml, 15.18 mmol) (4.0 M in dioxane) was slowly added. The mixture was stirred at rt for 16 h. Volatiles were stripped off and the residue was further dried under high vac to a dark oil (very hygroscopic). The residue was directly used in the next step.

Intermediate 33

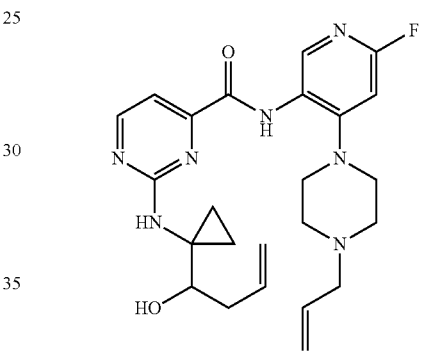

N-(4-(4-Allylpiperazin-1-yl)-6-fluoropyridin-3-yl)-2-((1-(1-hydroxybut-3-en-1-yl)cyclopropyl)amino)pyrimidine-4-carboxamide. In a 5 mL vial was N-(4-(4-allylpiperazin-1-yl)-6-fluoropyridin-3-yl)-2-chloropyrimidine-4-carboxamide (50 mg, 0.133 mmol) and 1-(1-aminocyclopropyl)but-3-en-1-ol hydrochloride (52.1 mg, 0.318 mmol) in NMP (0.4 mL) to give a tan solution. Hunig's base (0.093 mL, 0.531 mmol) was added. The mixture was heated at 120° C. for 2 h. LCMS showed good conversion to the desired product. The mixture was diluted with water and EtOAc. The layers were separated. The organic layer was washed with brine, dried and concentrated to a tan oil/solid. Purification by FCC up to 70% EtOAc/hexane afforded the desired product (25 mg, 40%) as a colorless oil: 1H NMR (500 MHz, Chloroform-d) δ 9.84 (s, 1H), 9.14 (s, 1H), 8.60 (d, J=5.0 Hz, 1H), 7.54 (d, J=5.0 Hz, 1H), 6.61 (d, J=1.5 Hz, 1H), 6.00-5.85 (m, 2H), 5.52 (s, 1H), 5.44-5.03 (m, 5H), 3.27 (t, J=7.1 Hz, 1H), 3.17-3.04 (m, 6H), 2.71 (t, J=4.6 Hz, 4H), 2.55-2.42 (m, 2H), 1.25-1.19 (m, 1H), 1.03-0.86 (m, 3H); 19F NMR (470 MHz, Chloroform-d) δ −69.54; MS (ESI) (m/z): 466.4 (M−H)+.

Example 34

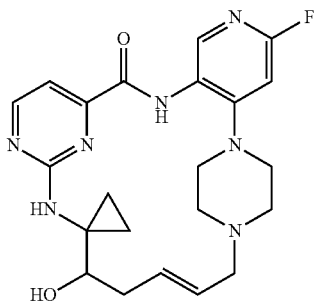 [SMILES: O=C1Nc2cnc(F)cc2N2CCN(C/C=C/CC(O)C3(CC3)Nc3nccc1n3)CC2]

Intermediate 35

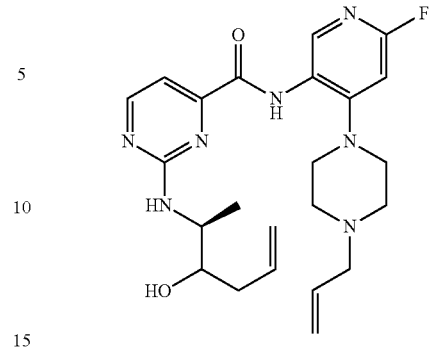

(E)-6'-fluoro-8'-hydroxyspiro[cyclopropane-1,7'-3,6-diaza-5(4,2)-pyrimidina-1(1,4)-piperazina-2(4,3)-pyridinacyclododecaphanen]-10'-en-4'-one. A solution of N-(4-(4-allylpiperazin-1-yl)-6-fluoropyridin-3-yl)-2-((1-(1-hydroxybut-3-en-1-yl)cyclopropyl)amino)pyrimidine-4-carboxamide (25 mg, 0.053 mmol), ClCH2CH2Cl (15 mL) in a 50 mL of round-bottom flask was degassed by a flow of N2 for 5 min. Zhan 1B catalyst (11.77 mg, 0.016 mmol) was added under nitrogen. It was then heated at 70° C. for 1.5 h. TLC (9/1 CH2Cl2/MeOH) showed good conversion to a slightly more polar spot. All volatiles were removed. The residue was subjected to purification by FCC up to 8% MeOH/CH2Cl2 to afford the desired product (12.7 mg, 54%) as a tan solid: Both 1H and 19F NMRs showed a mixture of isomers with a ratio of 3/1 (confirmed by HPLC analysis); MS (ESI) (m/z): 440.2 (M+H)$^+$.

N-(4-(4-Allylpiperazin-1-yl)-6-fluoropyridin-3-yl)-2-(((2S)-3-hydroxyhex-5-en-2-yl)amino)pyrimidine-4-carboxamide. In a 5 mL vial was N-(4-(4-allylpiperazin-1-yl)-6-fluoropyridin-3-yl)-2-chloropyrimidine-4-carboxamide (55 mg, 0.146 mmol) and (2S)-2-aminohex-5-en-3-ol hydrochloride (44.3 mg, 0.292 mmol) in NMP (0.4 mL) to give a tan solution. Hunig's base (0.076 mL, 0.438 mmol) was added. The mixture was heated at 120° C. for 3 h. LCMS showed good conversion to the desired product. The mixture was diluted with water and EtOAc. The layers were separated. The organic layer was washed with brine, dried and concentrated to a tan oil/solid. Purification by FCC up to 8% afforded the desired product (39 mg, 59%) as a light yellow oil. 1H NMR showed a mixture of two diastereomers. MS (ESI) (m/z): 456.3 (M+H)$^+$.

Example 36 and 37

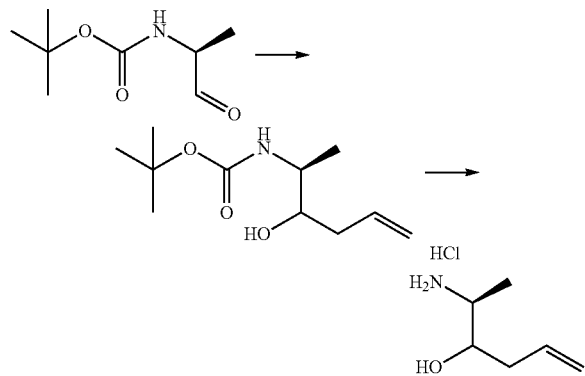

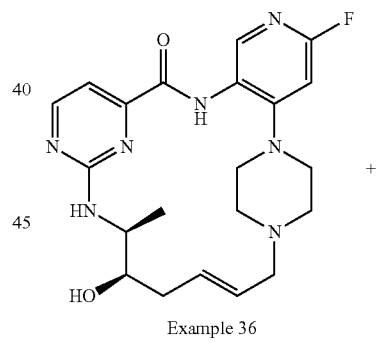

(2S)-2-Aminohex-5-en-3-ol hydrochloride. In a 100 mL round-bottomed flask was (S)-tert-butyl (1-oxopropan-2-yl)carbamate (446 mg, 2.57 mmol) in tetrahydrofuran (8 mL) to give a colorless solution. Allylmagnesium bromide (5.15 mL, 5.15 mmol) was slowly added. The mixture was stirred at rt for 1 h and was quenched with saturated NH4Cl solution. The layers were separated. The aqueous layer was extracted with EtOAc. The combined organic layers were washed with brine, dried and concentrated to a tan oil (560 mg, 100%). Crude 1H NMR indicated the desired product as a mixture of diastereomers. In a 100 mL round-bottomed flask was tert-butyl ((2S)-3-hydroxyhex-5-en-2-yl)carbamate (0.553 g, 2.57 mmol). HCl (3.86 ml, 15.42 mmol) (4.0 M in dioxane) was slowly added. The mixture was stirred at rt for 16 h. Volatiles were stripped off and the residue was further dried under high vac to a dark solid (very hygroscopic). The residue was used in the next step.

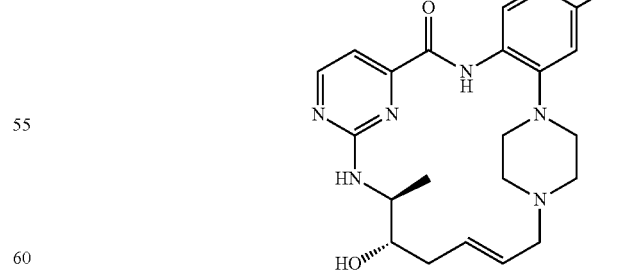

Example 37

(7S,8R,E)-2$^6$-fluoro-8-hydroxy-7-methyl-3,6-diaza-5(4,2)-pyrimidina-1(1,4)-piperazina-2(4,3)-pyridinacyclododecaphan-10-en-4-one (36) and (7S,8S,E)-2$^6$-fluoro-8-hydroxy-7-methyl-3,6-diaza-5(4,2)-pyrimidina-1(1,4)- piperazina-2(4,3)-pyridinacyclododecaphan-10-en-4-one (37). A solution of intermediate 35 (39 mg, 0.086 mmol), ClCH2CH2Cl (18 mL) in a 50 mL of round-bottom flask was degassed by a flow of N2 for 5 min. Zhan 1B catalyst (18.85 mg, 0.026 mmol) was added under nitrogen. It was then heated at 70° C. for 1.5 h. TLC (9/1 CH2Cl2/MeOH) showed good conversion to two more polar spots. All volatiles were removed. The residue was subjected to purification by FCC up to 8% MeOH/CH2Cl2 to afford the desired products 36 (9.5 mg, 26%) and 37 (10.5 mg, 29%) as tan oils (the alcohol configuration was tentatively assigned): 36: $^1$H NMR (500 MHz, Chloroform-d) δ 9.49 (s, 1H), 9.28 (s, 1H), 8.53 (d, J=4.7 Hz, 1H), 7.52 (d, J=4.7 Hz, 1H), 6.60 (d, J=1.5 Hz, 1H), 6.33 (s, 1H), 5.87-5.76 (m, 1H), 5.54 (s, 1H), 4.24 (s, 1H), 4.09 (d, J=11.1 Hz, 1H), 3.56-3.49 (m, 1H), 3.26-3.14 (m, 2H), 2.99-2.58 (m, 8H), 1.67 (s, 2H), 1.28 (d, J=3.0 Hz, 3H); 19F NMR (470 MHz, Chloroform-d) δ −70.13; MS (ESI) (m/z): 428.2 (M+H)$^+$. 37: 1H NMR (500 MHz, Chloroform-d) δ 9.71 (s, 1H), 9.21 (s, 1H), 8.56 (d, J=4.8 Hz, 1H), 7.52 (d, J=4.7 Hz, 1H), 6.61 (d, J=1.6 Hz, 1H), 5.89-5.65 (m, 3H), 4.30-4.18 (m, 1H), 3.92 (t, J=6.4 Hz, 1H), 3.50-3.41 (m, 1H), 3.31-3.17 (m, 3H), 2.95-2.62 (m, 7H), 1.71 (s, 2H), 1.32 (d, J=6.4 Hz, 3H); 19F NMR (470 MHz, Chloroform-d) δ −69.87; MS (ESI) (m/z): 428.2 (M+H)$^+$.

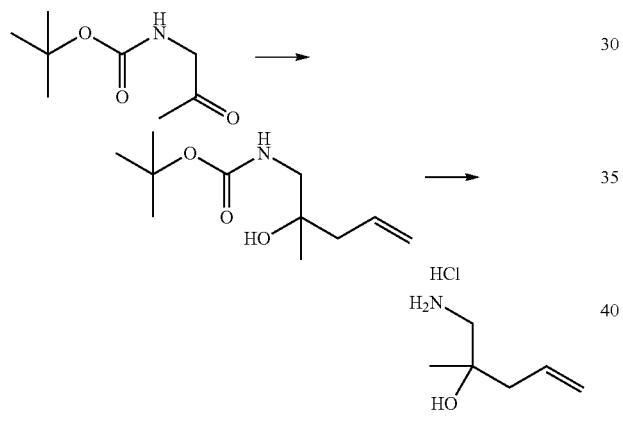

1-Amino-2-methylpent-4-en-2-ol hydrochloride. Ref. Mai, D. N.; Rosen, B. R.; Wolfe, J. P. Org. Lett. 2011, 13, 2932-2935. In a 100 mL round-bottomed flask was tert-butyl (2-oxopropyl)carbamate (451 mg, 2.60 mmol) in diethyl ether (8 mL) to give a colorless solution. Allylmagnesium bromide (5.73 mL, 5.73 mmol) was slowly added at rt. The mixture was stirred at rt for 2 h and was quenched with saturated NH4Cl solution. The layers were separated. The aqueous layer was extracted with EtOAc. The combined organic layers were washed with brine, dried and concentrated to a tan oil (crude 580 mg, 100%). Crude 1H NMR indicated the desired product: 1H NMR (500 MHz, Chloroform-d) δ 5.88 (ddt, J=17.6, 10.3, 7.5 Hz, 1H), 5.22-5.08 (m, 2H), 4.93 (s, 1H), 3.15 (d, J=6.3 Hz, 2H), 2.38 (s, 1H), 2.26 (ddt, J=7.4, 2.3, 1.1 Hz, 2H), 1.46 (s, 9H), 1.18 (s, 3H). In a 100 mL round-bottomed flask was tert-butyl (2-hydroxy-2-methylpent-4-en-1-yl)carbamate (560 mg, 2.60 mmol). HCl (3900 µl, 15.60 mmol) (4.0 M in dioxane) was slowly added. The mixture was stirred at rt for 2 h. Volatiles were stripped off and the residue was further dried under high vac to a dark oil (crude 390 mg, 99%, very hygroscopic). The residue was directly used in the next step.

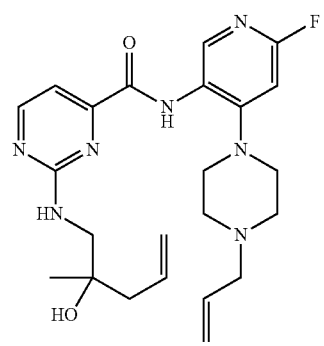

Intermediate 38

N-(4-(4-Allylpiperazin-1-yl)-6-fluoropyridin-3-yl)-2-((2-hydroxy-2-methylpent-4-en-1-yl)amino)pyrimidine-4-carboxamide. In a 5 mL vial was N-(4-(4-allylpiperazin-1-yl)-6-fluoropyridin-3-yl)-2-chloropyrimidine-4-carboxamide (50 mg, 0.133 mmol) and 1-amino-2-methylpent-4-en-2-ol hydrochloride (40.2 mg, 0.265 mmol) in NMP (0.3 mL) to give a tan solution. Hunig's base (0.070 mL, 0.398 mmol) was added. The mixture was heated at 100° C. for 16 h. LCMS showed the desired product. The mixture was diluted with water and EtOAc. The layers were separated. The organic layer was washed with brine, dried and concentrated to a tan oil/solid. Purification by FCC up to 8% MeOH/CH2Cl2 afforded the desired product (43 mg, 71%) as an off-white solid: 1H NMR (500 MHz, Chloroform-d) δ 9.90 (s, 1H), 9.13 (s, 1H), 8.56 (d, J=4.9 Hz, 1H), 7.44 (d, J=4.9 Hz, 1H), 6.60 (d, J=1.3 Hz, 1H), 5.98-5.81 (m, 2H), 5.68 (s, 1H), 5.27-5.07 (m, 4H), 3.60 (dd, J=6.0, 2.3 Hz, 2H), 3.14-3.03 (m, 6H), 2.71 (t, J=4.7 Hz, 4H), 2.40-2.34 (m, 2H), 1.90 (s, 1H), 1.30 (s, 3H); 19F NMR (470 MHz, Chloroform-d) δ −69.82; MS (ESI) (m/z): 456.3 (M+H)$^+$.

Example 39

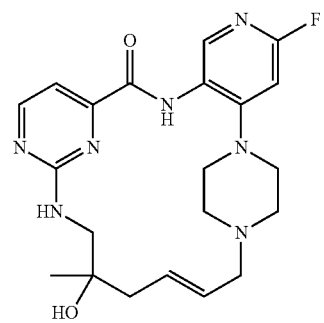 [SMILES: CC1(O)C/C=C/CN2CCN(CC2)c2cc(F)ncc2NC(=O)c2ccnc(n2)NC1]

(E)-2$^6$-Fluoro-8-hydroxy-8-methyl-3,6-diaza-5(4,2)-pyrimidina-1(1,4)-piperazina-2(4,3)-pyridinacyclododecaphan-10-en-4-one. A solution of intermediate 39 (40.8 mg, 0.090 mmol), ClCH2CH2Cl (20 mL) in a 50 mL of round-bottom flask was degassed by a flow of N2 for 5 min. Zhan 1B catalyst (19.72 mg, 0.027 mmol) was added under nitrogen. It was then heated at 70° C. for 1.5 h. TLC (9/1 CH2Cl2/MeOH) showed partial conversion to a more polar spot. All volatiles were removed. The residue was subjected to purification by FCC up to 8% MeOH/CH2Cl2 to afford the desired product (23.4 mg) as a tan solid, as well as recovered starting material (9 mg, 22%). TLC of the product showed some impurity. It was further purified by prep-HPLC to obtain the desired product with 99% purity (14.3 mg, 37%): 1H NMR (500 MHz, DMSO-d6) δ 9.65 (s, 1H), 8.91 (s, 1H), 8.62 (s, 1H), 7.33 (d, J=4.6 Hz, 1H), 6.93 (s, 1H), 6.47 (s, 1H), 5.78-5.54 (m, 2H), 5.02 (s, 1H), 3.15 (dd, J=13.4, 8.2 Hz, 2H), 2.97 (d, J=25.4 Hz, 4H), 2.76-2.68 (m, 4H), 2.40 (t, J=11.1 Hz, 1H), 2.30 (d, J=8.9 Hz, 1H), 1.24 (s, 3H) (missing 2H likely buried in the water peak); MS (ESI) (m/z): 428.3 (M+H)+.

Intermediate 40

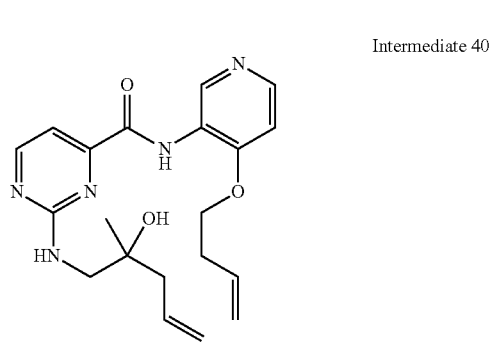 [SMILES: C=CCCOc1ccncc1NC(=O)c1ccnc(NCC(C)(O)CC=C)n1]

N-(4-(But-3-en-1-yloxy)pyridin-3-yl)-2-((2-hydroxy-2-methylpent-4-en-1-yl)amino)pyrimidine-4-carboxamide. In a 2 mL vial was N-(4-(but-3-en-1-yloxy)pyridin-3-yl)-2-chloropyrimidine-4-carboxamide (54.1 mg, 0.178 mmol) and 1-amino-2-methylpent-4-en-2-ol hydrochloride (53.8 mg, 0.355 mmol) in NMP (0.3 mL) to give a tan solution. Hunig's base (0.093 mL, 0.533 mmol) was added. The mixture was heated at 100° C. for 20 h. LCMS showed good conversion to the desired product. The mixture was diluted with water and EtOAc. The layers were separated. The organic layer was washed with brine, dried and concentrated to a tan oil. Purification by FCC up to 8% MeOH afforded the desired product (26.1 mg, 38%) as an off-white solid: 1H NMR (400 MHz, Chloroform-d) δ 10.14 (s, 1H), 9.69 (s, 1H), 8.54 (d, J=4.9 Hz, 1H), 8.31 (d, J=5.6 Hz, 1H), 7.43 (d, J=4.8 Hz, 1H), 6.85 (d, J=5.5 Hz, 1H), 5.94 (tdd, J=17.5, 9.9, 5.9 Hz, 2H), 5.73 (s, 1H), 5.33-5.11 (m, 4H), 4.21 (t, J=6.6 Hz, 2H), 3.63-3.49 (m, 2H), 2.69 (qt, J=6.7, 1.4 Hz, 2H), 2.41-2.31 (m, 2H), 2.09-1.96 (m, 1H), 1.29 (s, 3H); MS (ESI) (m/z): 384.2 (M+H)+.

Example 41

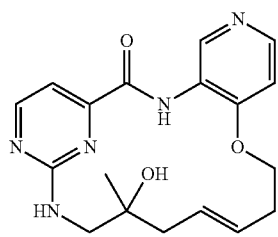 [SMILES: CC1(O)C/C=C/CCOc2ccncc2NC(=O)c2ccnc(n2)NC1]

(E)-11-Hydroxy-11-methyl-5-oxa-3,13-diaza-1(4,2)-pyrimidina-4(3,4)-pyridinacyclotridecaphan-8-en-2-one. A solution of intermediate 40 (25 mg, 0.065 mmol), ClCH2CH2Cl (15 mL) in a 50 mL of round-bottom flask was degassed by a flow of N2 for 5 min. Zhan 1B catalyst (14.35 mg, 0.020 mmol) was added under nitrogen. It was then heated at 70° C. for 1.5 h. TLC (9/1 CH2Cl2/MeOH) showed partial conversion (some SM left) to a more polar spot. All volatiles were removed. The residue was subjected to purification by FCC up to 8% MeOH/CH2Cl2 to afford the desired product (9.1 mg, 39%) as a tan solid: 1H NMR showed a mixture of two isomers with a ratio of around 2/1, which was conformed by analytical HPLC; MS (ESI) (m/z): 356.2 (M+H)+.

Example 42

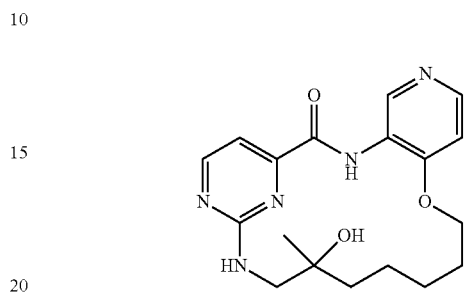

11-Hydroxy-11-methyl-5-oxa-3,13-diaza-1(4,2)-pyrimidina-4(3,4)-pyridinacyclotridecaphan-2-one. In a 50 mL round-bottomed flask was example 41 (6.4 mg, 0.018 mmol) and Pd/C (5.75 mg, 5.40 μmol) in MeOH (1 mL) to give a black suspension. The mixture was stirred under 1 atom hydrogen for 17 h. LCMS showed the desired product. The mixture was filtered and concentrated. The material was purified by prep-HPLC to afford the desired product (1.4 mg, 22%): 1H NMR (400 MHz, Methanol-d4) δ 9.63 (s, 1H), 8.52 (d, J=4.8 Hz, 1H), 8.21 (d, J=5.6 Hz, 1H), 7.57 (s, 1H), 7.37 (d, J=4.8 Hz, 1H), 7.02 (d, J=5.7 Hz, 1H), 4.30-4.20 (m, 2H), 3.79 (d, J=13.3 Hz, 1H), 3.44 (d, J=13.3 Hz, 1H), 3.32 (p, J=1.6 Hz, 1H), 1.97 (d, J=14.6 Hz, 2H), 1.92-1.52 (m, 7H), 1.27 (s, 3H); MS (ESI) (m/z): 358.2 (M+H)+.

Intermediate 43

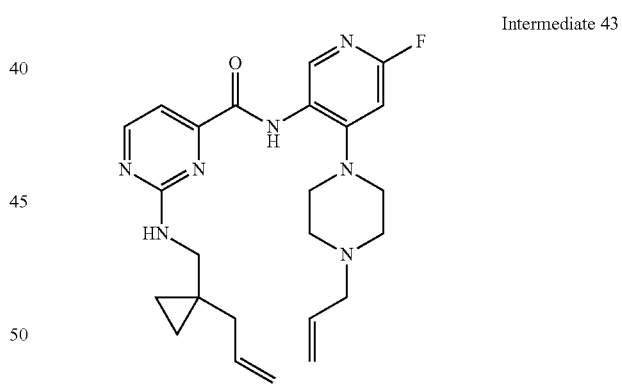

2-(((1-Allylcyclopropyl)methyl)amino)-N-(4-(4-allylpiperazin-1-yl)-6-fluoropyridin-3-yl)pyrimidine-4-carboxamide. In a 5 mL vial was N-(4-(4-allylpiperazin-1-yl)-6-fluoropyridin-3-yl)-2-chloropyrimidine-4-carboxamide (50 mg, 0.133 mmol) and (1-allylcyclopropyl)methanamine (29.5 mg, 0.265 mmol) in NMP (0.3 mL) to give a tan solution. Hunig's base (0.070 mL, 0.398 mmol) was added. The mixture was heated at 100° C. for 16 h. LCMS showed the desired product. The mixture was diluted with water and EtOAc. The layers were separated. The organic layer was washed with brine, dried and concentrated to a tan oil/solid. Purification by FCC up to 8% MeOH/CH2Cl2 afforded the desired product (49 mg, 82%) as an off-white solid: 1H NMR (400 MHz, Chloroform-d) δ 9.89 (s, 1H), 9.11 (s, 1H), 8.53 (d, J=4.8 Hz, 1H), 7.38 (d, J=4.8 Hz, 1H), 6.59 (d, J=1.5 Hz, 1H), 5.93-5.72 (m, 2H), 5.67-5.26 (m, 1H), 5.25-5.14 (m, 2H), 5.10-4.92 (m, 2H), 3.45 (d, J=5.4 Hz, 2H), 3.06 (dt, J=9.7, 5.6 Hz, 6H), 2.34 (t, J=8.1 Hz, 4H), 2.15 (dt, J=7.1, 1.3 Hz, 2H), 0.59-0.44 (m, 4H); 19F NMR (376 MHz, Chloroform-d) δ −69.96; MS (ESI) (m/z): 452.4 (M+H)$^+$.

Example 44

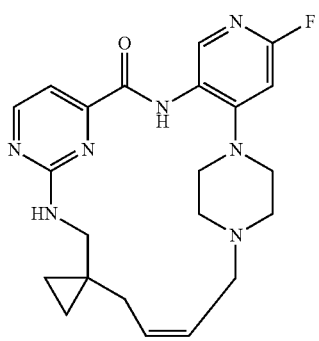 [SMILES: O=C1Nc2cnc(F)cc2N2CCN(C/C=C\CC3(CC3)CNc3nccc1n3)CC2]

(Z)-6'-fluorospiro[cyclopropane-1,8'-3,6-diaza-5(4,2)-pyrimidina-1(1,4)-piperazina-2(4,3)-pyridinacyclododecaphanen]-10'-en-4'-one. A solution of intermediate 43 (47 mg, 0.104 mmol), ClCH2CH2Cl (22 mL) in a 50 mL of round-bottom flask was degassed by a flow of N2 for 5 min. Zhan 1B catalyst (22.91 mg, 0.031 mmol) was added under nitrogen. It was then heated at 70° C. for 2 h. TLC (9/1 CH2Cl2/MeOH) showed good conversion to a more polar spot. All volatiles were removed. The residue was subjected to purification by FCC up to 8% MeOH/CH2Cl2 to afford the desired product (35 mg, 79%) as a black oil tar: $^1$H NMR (400 MHz, Chloroform-d) δ 10.15 (s, 1H), 9.15 (s, 1H), 8.56 (d, J=4.8 Hz, 1H), 7.44 (d, J=4.8 Hz, 1H), 6.62 (d, J=1.9 Hz, 1H), 5.83 (s, 1H), 5.72 (s, 1H), 5.37 (s, 1H), 3.45 (d, J=4.7 Hz, 2H), 3.40 (d, J=7.3 Hz, 2H), 3.11 (s, 2H), 2.93 (s, 4H), 2.82 (s, 2H), 2.29-2.14 (m, 2H), 0.68-0.52 (m, 4H); 19F NMR (376 MHz, Chloroform-d) δ −69.63; MS (ESI) (m/z): 424.3 (M+H)$^+$.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

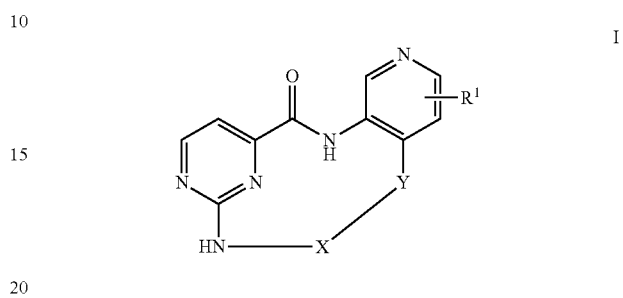

where:
R$^1$ is hydrogen, halo, alkyl, haloalkyl, alkoxy or haloalkoxy;
X is alkylene or alkenylene with 0-4 substituents selected from halo, alkyl, haloalkyl, hydroxy, alkoxy, haloalkoxy, and ($C_{3-7}$)-spirocycloalkyl; and
Y is O, piperazinyl, or morpholinyl;
or a pharmaceutically acceptable salt thereof.

2. A compound of claim 1 where Y is O.
3. A compound of claim 1 where Y is piperazinyl.
4. A compound of claim 1 where Y is morpholinyl.
5. A compound of claim 1 where X is ($C_{5-7}$)-alkylene.
6. A compound of claim 1 where X is ($C_{5-6}$)-alkenylene.
7. A pharmaceutical composition comprising a compound of claim 1 or a pharmaceutically acceptable salt thereof and a pharmaceutically acceptable carrier.
8. A method for the treatment of a condition selected from the group consisting of Alzheimer's disease, frontotemporal dementia, progressive supranuclear palsy, argyophilic grain disease, corticobasal degeneration, Pick's disease, Parkinson's disease, amyotrophic lateral sclerosis, stroke, Huntington's disease, and vascular dementia, which comprises administering to a patient in need thereof a therapeutically affective amount of a compound of claim 1.
9. The method of claim 8 directed to the treatment of Alzheimer's disease.

* * * * *